US012790285B2

(12) United States Patent
Suzuki et al.

(10) Patent No.: US 12,790,285 B2
(45) Date of Patent: Nov. 10, 2026

(54) [11C]-LABELED ACYCLIC RETINOID, CENTRAL NERVOUS SYSTEM ACTIVATOR, AND PRODUCTION METHODS FOR SAME

(71) Applicant: NATIONAL CENTER FOR GERIATRICS AND GERONTOLOGY, Obu City (JP)

(72) Inventors: Masaaki Suzuki, Obu City (JP); Kengo Ito, Obu City (JP); Yasuyuki Kimura, Obu City (JP); Aya Ogata, Obu City (JP); Hiroshi Ikenuma, Obu City (JP); Tetsuya Kimura, Obu City (JP); Nobuyuki Kimura, Obu City (JP); Hiroko Koyama, Gifu (JP); Hideki Ishii, Chiba (JP); Meiei Cho, Chiba (JP); Kazunori Kawamura, Chiba (JP); Takafumi Minamimoto, Chiba (JP); Yuji Nagai, Chiba (JP); Hiroshi Katsuki, Kumamoto (JP)

(73) Assignee: NATIONAL CENTER FOR GERIATRICS AND GERONTOLOGY, Obu City (JP)

( * ) Notice: Subject to any disclaimer, the term of this patent is extended or adjusted under 35 U.S.C. 154(b) by 697 days.

(21) Appl. No.: 18/037,946

(22) PCT Filed: Nov. 18, 2021

(86) PCT No.: PCT/JP2021/042503
§ 371 (c)(1),
(2) Date: May 19, 2023

(87) PCT Pub. No.: WO2022/107865
PCT Pub. Date: May 27, 2022

(65) Prior Publication Data
US 2024/0002313 A1 Jan. 4, 2024

(30) Foreign Application Priority Data
Nov. 20, 2020 (JP) ................................ 2020-193167

(51) Int. Cl.
*C07B 59/00* (2006.01)
*A61K 51/04* (2006.01)
(Continued)

(52) U.S. Cl.
CPC ........ *C07B 59/004* (2013.01); *A61K 51/0402* (2013.01); *A61P 25/00* (2018.01); *C07C 57/03* (2013.01); *C07B 2200/05* (2013.01)

(58) Field of Classification Search
CPC .................................................... C07B 59/004
See application file for complete search history.

(56) References Cited

U.S. PATENT DOCUMENTS 4,917,829 A 4/1990 Yamatsu et al.
6,369,251 B1 4/2002 Takano et al.
(Continued)

FOREIGN PATENT DOCUMENTS

JP 56-140949 A 11/1981
JP 2001-2621 A 1/2001
(Continued)

OTHER PUBLICATIONS

Johansson Seechurn, Carin CC, et al. "Palladium-catalyzed cross-coupling: a historical contextual perspective to the 2010 Nobel Prize." Angewandte Chemie International Edition 51.21 (2012): 5062-5085. (Year: 2012).*
(Continued)

*Primary Examiner* — Andrew D Kosar
*Assistant Examiner* — Connor K English
(74) *Attorney, Agent, or Firm* — Birch, Stewart, Kolasch & Birch, LLP

(57) ABSTRACT

[Object] Provided are a $^{11}C$-labeled acyclic retinoid that can be synthesized in a short time with a high yield and can be suitably used for PET for elucidating intracerebral kinetics, a PET probe using it, and methods for producing them.

[Solution] The $^{11}C$-labeled acyclic retinoid of the present invention is characterized by being represented by the following chemical formula (a). This compound can be produced by a coupling step of cross-coupling a methyl iodide labelled with $^{11}C$ and the following organotin compound (b) (provided that in the formula, $R^1$ and $R^2$ represent alkyl groups which may have a branch) in an aprotic solvent in the presence of a palladium complex, a phosphine ligand, and a cuprous halide.

(a)

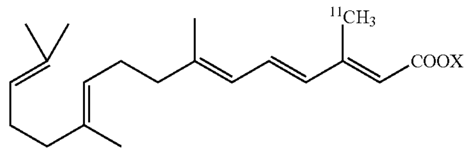

(b)

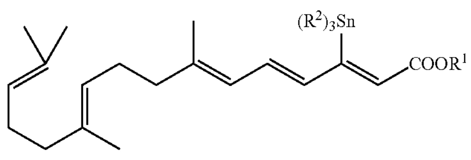

4 Claims, 9 Drawing Sheets

(51) Int. Cl.
*A61P 25/00* (2006.01)
*C07C 57/03* (2006.01)

(56) References Cited

U.S. PATENT DOCUMENTS

| | | | |
|---|---|---|---|
| 2004/0242690 | A1 | 12/2004 | Tanikawa et al. |
| 2013/0281736 | A1 | 10/2013 | Beumer |

FOREIGN PATENT DOCUMENTS

| | | | |
|---|---|---|---|
| JP | 2004-331654 | A | 11/2004 |
| JP | 2013-540762 | A | 11/2013 |
| WO | WO 2014/049366 | A1 | 4/2014 |
| WO | WO 2015/073072 | A1 | 5/2015 |

OTHER PUBLICATIONS

Lane, Michelle A., and Sarah J. Bailey. "Role of retinoid signalling in the adult brain." Progress in neurobiology 75.4 (2005): 275-293. (Year: 2005).*

Gribkoff, Valentin K., and Leonard K. Kaczmarek. "The need for new approaches in CNS drug discovery: Why drugs have failed, and what can be done to improve outcomes." Neuropharmacology 120 (2017): 11-19. (Year: 2017).*

Drummond, Eleanor, and Thomas Wisniewski. "Alzheimer's disease: experimental models and reality." Acta neuropathologica vol. 133,2 (2017): 155-175. doi:10.1007/s00401-016-1662-x (Year: 2017).*

Alavijeh, Mohammad S et al. "Drug metabolism and pharmacokinetics, the blood-brain barrier, and central nervous system drug discovery." NeuroRx : the journal of the American Society for Experimental Neuro Therapeutics vol. 2,4 (2005): 554-71. doi:10.1602/neurorx.2.4.554 (Year: 2005).*

Beheshti, "Chapter 35—All-trans retinoic acid in Alzheimer's disease", Diagnosis and Management in Dementia, Aug. 14, 2020, vol. 1, pp. 559-572, doi:10.1016/B978-0-12-815854-8.00035-5.

Fukasawa et al., "Preclinical and Clinical Studies of tamibarotene for treatment of Alzheimer's disease", Vitamins, 2017, vol. 91, No. 7, pp. 419-425, doi:10.20632/vso.91.7_419.

Honda et al., "Peretinoin, an acyclic retinoid, improves the hepatic gene signature of chronic hepatitis C following curative therapy of hepatocellular carcinoma", BMC Cancer, Apr. 15, 2013, vol. 13, Articles No. 191, pp. 1-13, doi:10.1186/1471-2407-13-191.

International Search Report for PCT/JP2021/042503 (PCT/ISA/210) mailed on Jan. 11, 2022.

Ogata, "Search for potential of acyclic retinoid as remedy for Alzheimer's (30-37)", Research and development cost for longevity medical treatment, 2018, https://www.ncgg.go.jp/ncgg-kenkyu/documents/30/30xx-37.pdf, https://www.ncgg.go.jp/ncgg-kenkyu/kadai30.html.

Shibahara et al., "Synthesis of $^{11}$C-Labeled RXR Partial Agonist 1-[(3,5,5,8,8- Pentamethyl-5,6,7,8-tetrahydronaphthalen-2-yl) amino]benzotriazole-5-carboxylic Acid (CBt-PMN) by Direct [$^{11}$C]Carbon Dioxide Fixation via Organolithiation of Trialkyltin Precursor and PET Imaging Thereof", Journal of Medicinal Chemistry, 2017, vol. 60, pp. 7139-7145.

Suzuki et al., "Synthesis of $^{11}$C-labeled retinoic acid, [$^{11}$C]ATRA, via an alkenylboron precursor by Pd(0)-mediated rapid C-[$^{11}$C]methylation", Bioorganic & Medicinal Chemistry Letters, Jun. 2, 2014, vol. 24, No. 15, pp. 3622-3625, doi:10.10161/j.bmcl.2014.05.041.

Suzuki, "Fast methylation reaction that renews the PET tracer synthesis base. Visualization of prostaglandin receptors", Kagaku to Seibutsu, 2005, vol. 43, No. 12, pp. 804-808, doi:10.1271/kagakutoseibutsu1962.43.804.

Takashima-Hirano et al., "Synthesis of [$^{11}$C]Am80 via Novel Pd(0)-Mediated Rapid [$^{11}$C] Carbonylation Using Arylboronate and [$^{11}$C]Carbon Monoxide", ACS Medicinal Chemistry Letters, 2012, vol. 3, pp. 804-807.

Written Opinion of the International Searching Authority for PCT/JP2021/042503 (PCT/ISA/237) mailed on Jan. 11, 2022.

* cited by examiner

EFFECT OF PERETINOIN ON THROMBIN-INDUCED BRAIN TISSUE DISORDERS

Mean ± S.E.M. *** P<0.001 by Dunn's multiple comparisons test.

Mean ± S.E.M. *** P<0.001 by Dunn's multiple comparisons test.

1 μM peretinoin 3　　10 μM peretinoin 3　　10 μM ATRA

RED; MAP2 (NERVE CELLS)　　GREEN; NESTIN (UNDIFFERENTIATED CELLS)

EVALUATION OF REACTIVITY TO NMDA

[11C]-LABELED ACYCLIC RETINOID, CENTRAL NERVOUS SYSTEM ACTIVATOR, AND PRODUCTION METHODS FOR SAME

TECHNICAL FIELD

The present invention relates to a [$^{11}$C]-labeled acyclic retinoid, a central nervous system activator, and methods for producing them. Since the [$^{11}$C]-labeled acyclic retinoid of the present invention has intracerebral migration, it can be suitably used as a PET probe for studying intracerebral kinetics of acyclic retinoids. Further, the central nervous system activator of the present invention contains an acyclic retinoid, which is an unlabeled body of the [$^{11}$C]-labeled acyclic retinoid of the present invention, and has an effect of migrating into a brain and activating a central nervous system. Therefore, it can be used as a therapeutic agent for central nervous system degenerative diseases and a lead compound for development thereof. Here, the "central nervous system degenerative disease" refers to all diseases caused by degeneration of a central nerve (for example, Alzheimer-type dementia, frontotemporal dementia, Lewy body dementia, Parkinson's disease, progressive supranuclear palsy, Huntington's disease, argyrophilic grain dementia, senile dementia of the neurofibrillary tangle type, and brain tumors), and is a concept including cerebrovascular diseases such as degeneration of the central nerve due to intracerebral hemorrhage.

BACKGROUND ART

All-trans-retinoic acid (ATRA) is a type of cyclic retinoid having a six-membered carbon skeleton, and is known to act as a ligand of a retinoic acid receptor in a nucleus and exhibit anticancer activity. Furthermore, it has been reported that the ATRA and artificial analogs thereof exhibit an improving effect on Alzheimer's disease (AD), which has attracted great attention.

[Chemical formula 1]

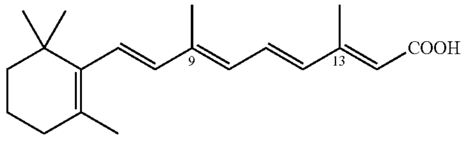

all-trans Retinoic acid

In order to develop a therapeutic drug targeting a brain for AD and the like, it is important to analyze intracerebral kinetics of a candidate compound for drug discovery, and positron emission tomography (PET) is extremely effective as means therefor. Therefore, the present inventors have published a study in which ATRA labeled with $^{11}$C is synthesized and used as a probe for PET (Non Patent Literature 1).

However, it has become clear that there are many problems as follows in using the $^{11}$C-labeled ATRA as a probe for PET.

1) There are many steps for synthesizing a labeled precursor. 2) The $^{11}$C-labeled ATRA is unstable under light or labeling reaction conditions. 3) A plurality of geometric isomers are generated in a $^{11}$C labeling process, and separation and purification thereof are complicated. 4) A large number of metabolites are generated in vivo, which makes intracerebral kinetics analysis complicated.

In order to solve these problems, some $^{11}$C-labeled artificial retinoids having a structure similar to ATRA and being relatively chemically stable have also been synthesized. For example, in Non Patent Literature 2, $^{11}$C-labeled Am80 was synthesized as a $^{11}$C-labeled artificial retinoid. However, when the $^{11}$C-labeled Am80 was used as a PET probe, no intracerebral migration was observed, and intracerebral kinetics analysis could not be conducted. Further, in Non Patent Literature 3, when $^{11}$C-labeled CBt-PMN was synthesized as a $^{11}$C-labeled artificial retinoid and used as a PET probe thereof, higher intracerebral migration than that of $^{11}$C-labeled bexarotene was observed. However, since a final yield in a case of total synthesis of the $^{11}$C-labeled CBt-PMN is as extremely low as 0.33%, image photographing by PET is used only for small animals, and intracerebral kinetics such as analysis of kinetics and intracerebral distribution has not been elucidated.

[Chemical formula 2]

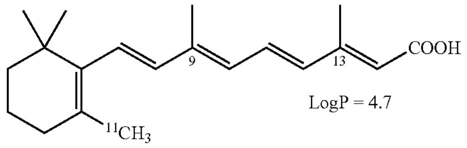

LogP = 4.7

[$^{11}$C]all-trans Retinoic acid

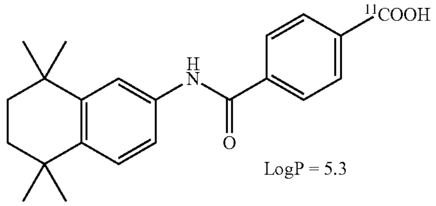

LogP = 5.3

[$^{11}$C]Am80

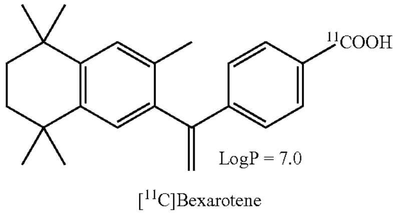

LogP = 7.0

[$^{11}$C]Bexarotene

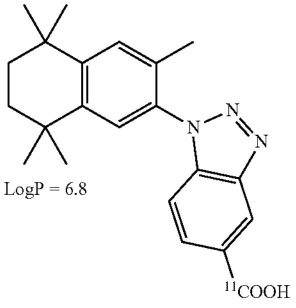

LogP = 6.8

[$^{11}$C]CBt-PMN

Note that Patent Literature 1 describes that peretinoin, which is a type of acyclic retinoid, can be used for anticancer agents. However, it has not been known at all so far that the peretinoin has intracerebral migration, and it has not been known either that the peretinoin activates a central nervous system (CNS) or can be used as an agent for central nervous system degenerative diseases. Further, conventionally known synthesis of the peretinoin requires many steps and takes time and effort.

CITATIONS LIST

Patent Literature

Patent Literature 1: JP S56-140949 A

Non-Patent Literature

Non Patent Literature 1: Suzuki M, Takashima-Hirano M, Ishii H, Watanabe C, Sumi K, Koyama H, Doi H. Bioorg Med Chem Lett. 2014; 243:3622-3625.

Non Patent Literature 2: Takashima-Hirano M, Ishii H, Suzuki M. ACS Med Chem Lett. 2012; 3:804-807.

Non Patent Literature 3: O. Shibahara, M. Watanabe, S. Yamada, M. Akehi, T. Sasaki, A. Akahoshi, T. Hanada, H. Hirano, S. Nakatani, H. Nishioka, Y. Takeuchi, H. Kakuta, J. Med. Chem. 2017, 60, 7139-7145.

SUMMARY OF INVENTION

Technical Problems

The present invention has been made in view of the conventional problems described above, and an object of the present invention is to achieve any one of the following 1) and 2).

1) To provide a $^{11}C$-labeled acyclic retinoid that can be synthesized in a short time with a high yield and can be suitably used as a PET probe for elucidating intracerebral kinetics, a PET probe using it, and methods for producing them.

2) To provide a new method for producing an acyclic retinoid and a central nervous system activator containing the acyclic retinoid.

Solutions to Problems

In order to solve the conventional problems described above, the present inventors have focused on acyclic retinoids having a chain-like carbon skeleton. Peretinoin, a type of acyclic retinoid, is known as a therapeutic drug for peripheral liver cancer, but there has been no reported example of acyclic retinoids migrating into a brain nor $^{11}C$-labeled acyclic retinoids. However, the acyclic retinoids have a ring-opened structure of a cyclic retinoid, and they are related to each other in terms of a chemical structure. Therefore, an attempt was made to label the acyclic retinoids with $^{11}C$ and use them as a PET probe, instead of the cyclic retinoids.

[Chemical formula 3]

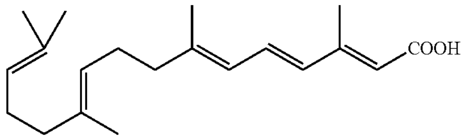

peretinoin

As a result, it was surprisingly found that the acyclic retinoids migrated into the brain, and it was found to be suitable for elucidating the intracerebral kinetics. Moreover, these $^{11}C$-labeled acyclic retinoids also have an advantage of being easier to synthesize and more chemically stable than the cyclic retinoids.

In other words, a $^{11}C$-labeled acyclic retinoid of the present invention includes a compound represented by the following chemical formula (a) (in other words, peretinoin in which a methyl group at the 3-position is labeled with $^{11}C$), or an ester or a salt thereof.

[Chemical formula 4]

(a)

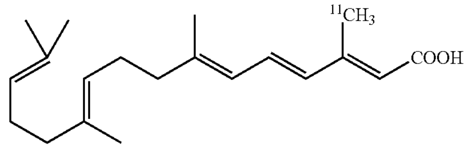

A PET probe of the present invention is characterized by containing the $^{11}C$-labeled acyclic retinoid of the present invention described above. According to test results of the present inventors, since this PET probe has intracerebral migration, it can be used as a PET probe for elucidating intracerebral kinetics. The $^{11}C$-labeled acyclic retinoid of the chemical formula (a) having a carboxy group has a higher intracerebral migration rate than the $^{11}C$-labeled acyclic retinoid in which the carboxy group is esterified, and is particularly excellent as a PET probe.

The $^{11}C$-labeled acyclic retinoid of the present invention can be produced by cross-coupling a methyl iodide labeled with $^{11}C$ and the following organotin compound (b) (provided that in the formula, —$COOR^1$ represents an ester group, and $R^2$ represents an alkyl group which may have a branch) in an aprotic solvent in the presence of a palladium complex, a phosphine ligand, and a cuprous halide. Furthermore, a carboxylic acid can be easily obtained by continuously hydrolyzing an ester group of a coupling product in the same reaction vessel. A strong base such as a potassium hydroxide and a sodium hydroxide can be used for the hydrolysis, and an acid such as a formic acid is added after the hydrolysis to obtain a free carboxylic acid.

[Chemical formula 3]

(b)

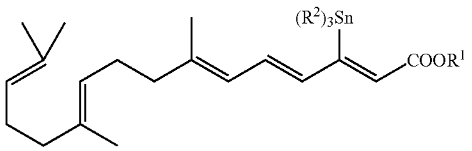

In this production method, the phosphine ligand is sterically coordinated to the palladium complex in an unsaturated manner to create an active reaction field, and further, the methyl iodide labeled with $^{11}C$ is oxidatively added to the palladium complex to which the phosphine ligand is coordinated to form a palladium complex in which the phosphine ligand is coordinated to $[^{11}C]CH_3PdI$.

On the other hand, the organotin compound (b) undergoes transmetalation with the cuprous halide to become an organocopper compound having high nucleophilicity.

Then, the palladium complex in which the phosphine ligand is coordinated to $[^{11}C]CH_3PdI$ undergoes a substitution reaction with the organocopper compound, further a reductive elimination occurs, and a coupling reaction with $[^{11}C]CH_3$ is completed.

The palladium complex is not particularly limited, and for example, a palladium zero-valent complex obtained by reducing $Pd(OAc)_2$, $Pd_2(dba)_3$, or the like can be used.

In addition, in the present description, the phosphine ligand refers to a compound having three organic substituents bonded to a trivalent phosphorus atom and further having an unshared electron pair. Specifically, examples of the phosphine ligand include trialkylphosphine such as trimethylphosphine, trioctylphosphine, tributylphosphine, and dimethyloctylphosphine, tri(o-tolyl)phosphine, tricyclohexylphosphine, trixylylphosphine, trimesitylphosphine, tris(tetramethylphenyl)phosphine, diphenyl-p-chlorophenylphosphine, tris(p-methoxyphenyl)phosphine, diphenylethylphosphine, dimethylphenylphosphine, bis(diphenylphosphino)methane, 1,2-bis(diphenylphosphino)ethane, dioctyloctoxyphosphine, dibutylbutoxyphosphine, diphenylphenoxyphosphine, ditolyltolyloxyphosphine, dixylylxylyloxyphosphine, diphenylethoxyphosphine, diethylphenoxyphosphine, octyldioctoxyphosphine, butylbutoxyphosphine, phenyldiphenoxyphosphine, tolylditolyloxyphosphine, xylyldixylyloxyphosphine, phenyldiethoxyphosphine, ethyldiphenoxyphosphine, trioctylphosphite, tributylphosphite, dimethyloctylphosphite, tricyclohexylphosphite, triphenylphosphite, tritolylphosphite, trixylylphosphite, diphenylethylphosphite, dimethylphenylphosphite, 1,3-bis(diphenylphosphino)propane (dppp), (2-biphenylyl)dicyclohexylphosphine, and tri-(1-naphthyl)phosphine.

As the aprotic solvent, a formamide solvent such as N,N-dimethylformamide and N,N-diethylformamide, an acetamide solvent such as N,N-dimethylacetamide and N,N-diethylacetamide, a pyrrolidone solvent such as N-methyl-2-pyrrolidone and N-vinyl-2-pyrrolidone, a sulfoxide solvent such as dimethylsulfoxide and diethylsulfoxide, hexamethylphosphoramide, γ-butyrolactone, and the like can be used. Among these, the formamide solvent, the acetamide solvent, and a pyrrolidone polar solvent are preferable.

Further, it is preferable to add at least one of a carbonate, an alkali metal fluoride, and an alkali metal salt of ascorbic acid in a coupling step. In this case, a trialkyltin halide produced as a by-product in the coupling step reacts with at least one of the carbonate, the alkali metal fluoride, and the alkali metal salt of ascorbic acid to neutralize or precipitate (precipitate as a trialkylstannyl carbonate in a case of the carbonate, as a trialkylstannyl fluoride in a case of the alkali metal fluoride, and as an ascorbate in a case of the alkali metal salt of ascorbic acid), and is thus excluded from a reaction system. Therefore, transmetalation from Sn to Cu is promoted, and a yield can also be increased.

A central nervous system activator of the present invention contains an acyclic retinoid (common name: peretinoin) represented by the following chemical formula (c), or an ester or a salt thereof as an active ingredient.

[Chemical formula 6]

(c)

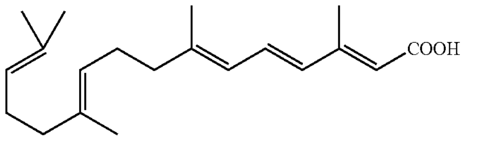

Since the $^{11}C$-labeled acyclic retinoid of the present invention has the intracerebral migration, peretinoin which is not labeled with $^{11}C$, or an ester or a salt thereof similarly has the intracerebral migration. Furthermore, according to the test results of the present inventors, the peretinoin which is the acyclic retinoid represented by the above chemical formula (c) and the ester thereof improve a motor function of a mouse after cerebral hemorrhage as well as suppress activity of microglia around a hematoma. From these facts, the peretinoin which is the acyclic retinoid represented by the above chemical formula (c), or the ester or the salt thereof can be used as a central nervous system (CNS) activator. Furthermore, it can be used in a therapeutic agent for central nervous system degenerative diseases, and can promote development of a new diagnostic and therapeutic drug as a lead compound for developing a therapeutic agent for central nervous system degenerative diseases.

A method for producing an acyclic retinoid of the present invention includes converting a phosphonic acid ester represented by the following chemical formula (d) (wherein $R^1$ represents an alkyl group) and a carboxylic acid ester represented by the following chemical formula (e) into an acyclic retinoid of a chemical formula (f) (wherein $—COOR^2$ represents an ester group) by the Horner-Wadsworth-Emmons reaction.

[Chemical formula 7]

(d)

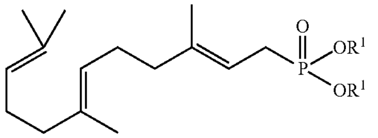

(e)

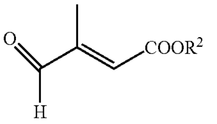

(f)

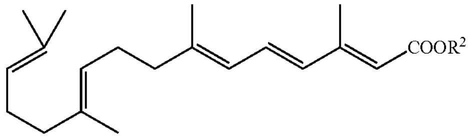

The phosphonic acid ester of the chemical formula (d) used in this production method can be easily obtained with a high yield by the Michaelis-Albuzov reaction using trans, trans-farnesol as a starting material, converting a hydroxyl group thereof into a chloride, and further using a trimethyl acid. Further, the carboxylic acid ester represented by the chemical formula (e) can be obtained while maintain the E configuration by converting hydroxyacetone into a hydroxyester of an E isomer by the Wittig olefin synthesis, and oxidizing it. Then, according to the production method of the present invention, the phosphonic acid ester of the following chemical formula (d) and an aldehyde of the chemical formula (e) are bonded with a carbon-carbon double bond by the HWE reaction, whereby the acyclic retinoid of the chemical formula (f) can be produced in fewer steps than the production method described in Patent Literature 1.

Furthermore, by hydrolyzing the acyclic retinoid of the chemical formula (f) thus obtained, the peretinoin can be obtained with a high stereoselective yield. For the hydrolysis, a strong base such as potassium hydroxide or sodium hydroxide can be used. After the hydrolysis, an acid such as a formic acid is added to obtain a free carboxylic acid.

Advantageous Effects of Invention

The $^{11}C$-labeled acyclic retinoid obtained by the production method of the present invention has sufficient radioactivity to obtain a PET image, and can be used as a PET probe. Further, since the $^{11}C$-labeled acyclic retinoid of the present invention has a $^{11}C$-labeled position that is metabolically stable, a PET probe with high reproducibility and high quality is provided. Furthermore, since the hydrolysis of the ester group after the coupling step proceeds quickly and easily, synthesis by using a general automated radiopharmaceutical synthesis device is possible. Further, since the $^{11}C$-labeled acyclic retinoid of the present invention has cerebral migration, it serves as a useful support molecular tool in a process of developing a therapeutic agent for central nervous system degenerative diseases, for example, promoting development of a new diagnostic and therapeutic drug for intracerebral cancers of acyclic retinoids targeting glioma, which is a cancer of a central nervous system.

In addition, since the central nervous system activator of the present invention has an effect of migrating into the brain and activating the central nervous system, it can be used as a therapeutic agent for central nervous system degenerative diseases and a lead compound for development thereof.

BRIEF DESCRIPTION OF DRAWINGS

FIG. 10 is a graph showing a rate of cerebral cortex cell death induced by K252a.

FIG. 11 is a graph showing a rate of striatal tissue atrophy induced by K252a.

DESCRIPTION OF EMBODIMENTS

Figure 1:
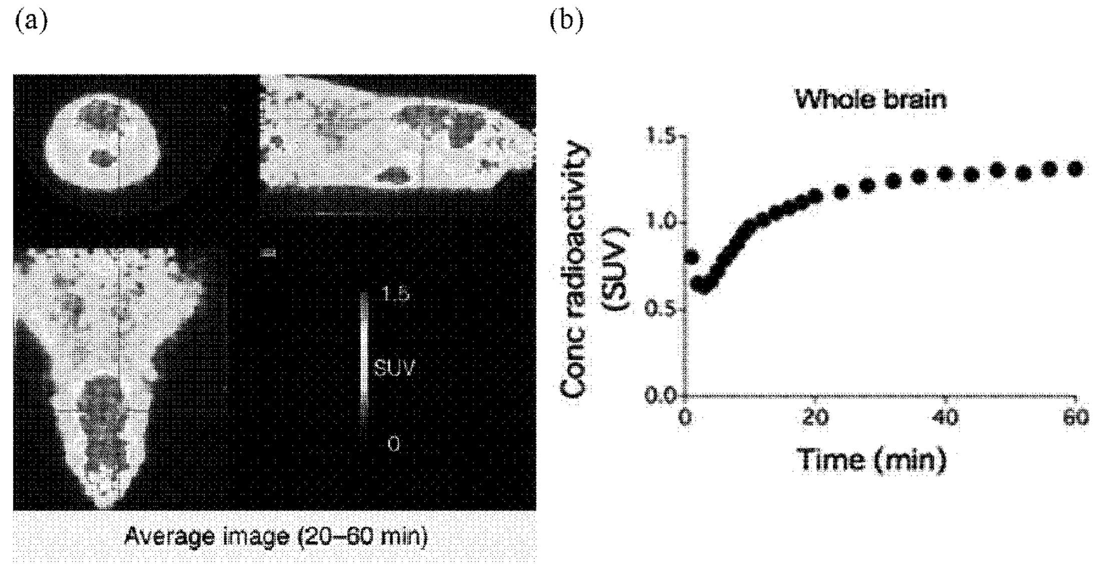
FIG. 1 is a PET image (a) and a graph (b) of radioactivity in a brain when $^{11}C$-labeled peretinoin [$^{11}C$]-3 was administered to a rat.

Acyclic retinoids 4a, 4b, and 4c and peretinoin 3 (see the following chemical formulae), and their $^{11}C$-labeled compounds [$^{11}C$]-4a, [$^{11}C$]-4b, [$^{11}C$]-4c, and [$^{11}C$]-3 were synthesized through the following procedure. Note that the acyclic retinoids 4a, 4b, and 4c and the peretinoin 3 are acyclic retinoids contained in a central nervous system activator of the present invention, and the [$^{11}C$]-4a, [$^{11}C$]-4b, [$^{11}C$]-4c, and [$^{11}C$]-3 are $^{11}C$-labeled acyclic retinoids of the present invention. Details will be described below.

[Chemical formula 8]

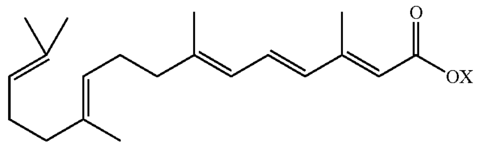

4a: X = Methyl
4b: X = Ethyl
4c: X = benzyl

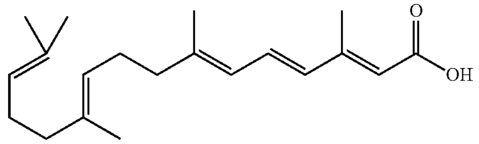

3

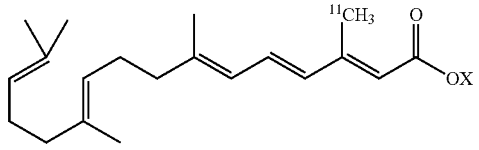

[$^{11}C$]-4a: X = Methyl
[$^{11}C$]-4b: X = Ethyl
[$^{11}C$]-4c: X = benzyl

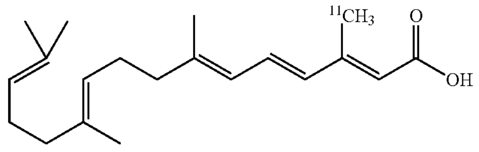

[$^{11}C$]-3

(Chemicals, Analyzers, and the Like Used in Examples)

All chemical substances and solvents except THF were purchased from Sigma-Aldrich Japan, Wako Pure Chemical Industries, Tokyo Chemical Industry, Kanto, and Nacalai Tesque and used as they were without purification. $^{1}H$, $^{13}C$, and $^{19}F$ nuclear magnetic resonance (NMR) spectra were measured with a JEOL JNM 400-400 spectrometer. A chemical shift was set to 0.00 ppm based on TMS, and set to 7.26 for $^{1}H$ NMR and 77.0 for $^{13}C$ NMR based on $CHCl_3$.

Abbreviations s, d, t, q, and m denote singlet, doublet, triplet, quartet, and multiplet, respectively. High resolution mass spectra (HRMS) were measured with a PE Biosystems Mariner system and a JEOL JMS-700/GI. [$^{11}$C]$CO_2$ was produced by the $^{14}N(p,\alpha)^{11}C$ nuclear reaction using a YPRIS HM-18 cyclotron (manufactured by Sumitomo Heavy Industries, Ltd.). For production of [$^{11}$C]methyl iodide and $^{11}$C-labeled compounds, a unique automated radiolabeling system consisting of heating, dilution, HPLC injection, fractional recovery, and evaporation of a reaction mixture was used. Radioactivity was quantified with an ATOMLABTM500 dose calibrator (Biodex Medical Systems, Inc.). As an analytical HPLC system used for a [$^{11}$C]methylated product, an HPLC system equipped with an amplifier and bias power supply 925-SCINT (AMETEK Co., Ltd.), a linear count rate meter 7131-1 (Ohyo Koken Kogyo Co. Ltd.), a Shimadzu system controller (SPD-10Avp), an online degasser (DGU-12A), a solvent delivery unit (LC-10ATvp), a column oven (CTO-10A), and a photodiode array detector (SCL-10Avp), and software (LC solution) were employed. As columns used for analytical and preparative HPLC, CAPCELL PAK C18 4.6×250 mm and CAPCELL PAK C18 MG 5 μm 10×250 mm (manufactured by Shiseido Company, Limited) were used.

Synthesis of $^{11}$C-labeled acyclic retinoid

An acyclic retinoid 14a and an acyclic retinoid 14b were synthesized by the following synthesis method.

[Chemical formula 9]

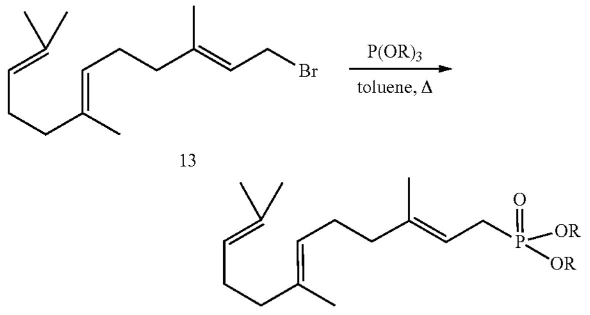

13

R = $CH_3$: 14a, 82%
R = $CH_2CH_3$: 14b, 82%

Synthesis of (2E,6E)-3,7,11-trimethyl-2,6,10-(dodecatrienyl)phosphonic acid diethyl ester 14b Trans, trans-farnesyl bromide 13 (2.7 mL, 10 mmol), triethyl phosphite (1.9 mL, 11 mmol), and dry toluene (20 mL) were put in a 50 mL round-bottom flask. A mixture was refluxed for 20 hours and then returned to room temperature. A solution was concentrated under reduced pressure, and a residue was purified by silica gel column chromatography (hexane/acetone=5:1 to ½) to obtain the compound 14b (2.82 g, 8.23 mmol, 82%) as a yellow oil.

$^1$H NMR (400 MHz, $CDCl_3$), 1.30 (t, J=7.0 Hz, 6H, $2CH_3$), 1.59 (s, 6H, $2CH_3$), 1.65 (d, J=3.6 Hz, 3H, $CH_3$), 1.67 (s, 3H, $CH_3$), 1.89-2.14 (m, 8H, $4CH_2$), 2.56 (dd, J=7.6, $^2J(^1H-^{31}P)$=21.6 Hz, 2H, $CH_2$), 4.00-4.16 (m, 4H, $2CH_2$), 5.03-5.13 (m, 2H, 2C═CH), 5.14-5.24 (m, $^1$H, C═CH); $^{13}$C NMR (100 MHz, $CDCl_3$), 16.06, 16.40, 16.56 (d, $^3J(^{13}C-^{31}P)$=5.7 Hz, 2C), 17.76, 25.76, 26.49, 26.53, 26.46 (d, $1J(^{13}C-^{31}P)$=139.2 Hz), 26.81, 39.78, 61.81 (d, $^2J(^{13}C-^{31}P)$=5.8 Hz, 2C), 112.51 (d, $^2J(^{13}C-^{31}P)$=11.5 Hz), 123.88, 124.39, 131.39, 135.37, 140.34 (d, $^3J(^{13}C-^{31}P)$=13.4 Hz); HR-MS (EI+,100% acetone): m/z: calcd for $C_{19}H_{35}O_3P$ ($[M-C_4H_9]^+$) 342.2324; found, 342.2319.

The compound 14a was obtained by a method similar to the method for synthesizing the compound 14b, using trimethyl phosphite instead of triethyl phosphite.

The compounds 4a, 4b, and 4c were synthesized by the following synthesis method.

[Chemical formula 10]

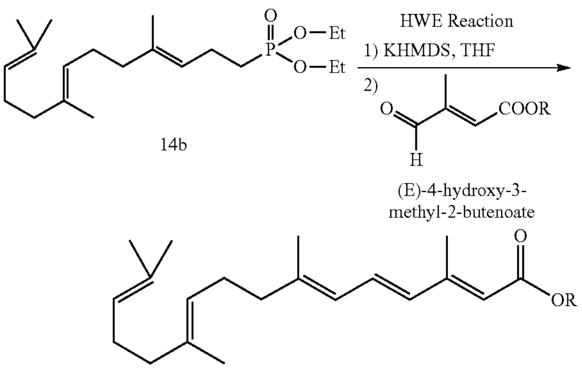

14b (E)-4-hydroxy-3-methyl-2-butenoate

4a: R = Me
4b: R = Et

Synthesis of acyclic retinoids 4a and 4b

Synthesis of (2E,4E,6E,10E)-3,7,11,15-tetramethyl-2,4,6,10,14-hexadecapentaenoic acid ethyl ester 4b An (E)-3-methyl-4-oxo-2-butenoic acid ethyl ester was synthesized from an (E)-4-hydroxy-3-methyl-2-butenoic acid ethyl ester (72.2 mg, 0.500 mmol) based on a known document (G. E. Magoulas, et. al. J. Med. Chem. 2011, 46, 721-737). The (E)-3-methyl-4-oxo-2-butenoic acid ethyl ester thus obtained was used without purification. The compound 14b (171 mg, 0.500 mmol) and dry THF (2 mL) were put in a 30 mL two-neck round-bottom flask and cooled to −78° C. in a dry ice/acetone bath, and at this temperature, bis(trimethylsilyl)amide potassium (1.0 M THF solution, 500 μL, 0.5 mmol) was added. A reaction mixture was stirred for 1 hour, and then the (E)-3-methyl-4-oxo-2-butenoic acid ethyl ester dissolved in THF (2 mL) was dropped at −78° C. After stirred at room temperature for 1 hour, an obtained mixture was cooled to 0° C., saturated aqueous $NH_4Cl$ (2 mL) was added, and the mixture was extracted with diethyl ether (3×5 mL). An organic layer was washed with water (10 mL) and dried with anhydrous sodium sulfate, and then a solvent was distilled off under reduced pressure. A crude product was purified by the silica gel column chromatography {hexane/ethyl acetate=50:1} to obtain an acyclic retinoid 4b (43 mg, 0.13 mmol, 26%) as a yellow oil.

$^1$H NMR (400 MHz, $CDCl_3$), 1.27 (t, J=7.2 Hz, 3H, $CH_3$), 1.58 (s, 3H, $CH_3$), 1.59 (d, J=0.8 Hz, 3H, $CH_3$), 1.66 (d, J=0.8 Hz, 3H, $CH_3$), 1.84 (d, J=0.8 Hz, 3H, $CH_3$), 1.90-2.20 (m, 8H, $4CH_2$), 2.31 (d, J=1.2 Hz, 3H, $CH_3$), 4.15 (q, J=7.2 Hz, 2H, $CH_2$), 5.00-5.20 (m, 2H, 2C═CH), 5.73 (s, 1H, C═CH), 5.95 (d, J=11.2 Hz, 1H, C═CH), 6.16 (d, J=15.6 Hz, 1H, C═CH), 6.83 (dd, J=15.6 11.2, Hz, 1H, C═CH);

$^{13}C$ NMR (100 MHz, $CDCl_3$), 13.88, 14.44, 16.10, 17.24, 17.77, 25.78, 26.49, 26.77, 39.76, 40.33, 59.67, 118.12, 123.62, 124.35, 125.02, 131.10, 131.43, 133.52, 135.70, 143.97, 153.09, 167.33; HR-MS (EI+, 100% acetone): m/z: calcd for $C_{22}H_{34}C_2([M-C_4H_9]^+)$ 330.2559; found, 330.2561.

Synthesis of (2E,4E,6E,10E)-3,7,11,15-tetramethyl-2,4,6,10,14-hexadecapentaenoic acid ethyl ester 4a A compound (4a) was synthesized from the compound 14b (35.5 mg, 0.104 mmol) and an (E)-3-methyl-4-oxo-2-butenoic acid methyl ester ((E)-4-hydroxy-3-methyl-2-butenoic acid. The procedure was performed in the same manner as the method for synthesizing the acyclic retinoid (4b), and a compound 4a (18.0 mg, 56.9 μmol, 55%) was obtained as a yellow oil.

$^1H$ NMR (400 MHz, $CDCl_3$), 1.58 (s, 3H, $CH_3$), 1.59 (d, J=0.8 Hz, 3H, $CH_3$), 1.66 (s, 3H, $CH_3$), 1.84 (s, 3H, $CH_3$), 1.90-2.20 (m, 8H, $4CH_2$), 2.32 (d, J=0.8 Hz, 3H, $CH_3$), 3.69 (s, 3H, $CH_3$), 5.00-5.20 (m, 2H, 2C═CH), 5.73 (s, 1H, C═CH), 5.95 (d, J=11.6 Hz, 1H, C═CH), 6.17 (d, J=14.8 Hz, 1H, C═CH), 6.83 (dd, J=14.8, 11.6 Hz, 1H, C═CH); $^{13}C$ NMR (100 MHz, $CDCl_3$), 13.90, 16.10, 17.26, 17.77, 25.78, 26.49, 26.77, 39.76, 40.33, 51.01, 117.58, 123.61, 124.35, 125.00, 131.29, 131.45, 133.43, 135.71, 144.15, 153.43, 167.75; HR-MS (EI+, 100% acetone): m/z: calcd for $C_{21}H_{32}O_2$ ($M^+$) 316.2402; found, 316.2415.

Synthesis of (2E,4E,6E,10E)-3,7,11,15-tetramethyl-2,4,6,10,14-hexadecapentaenoic acid benzyl ester 4c An 4,5-Didehydrogeranylgeranoic acid (18.2 mg, 60.2 μmol) and dry DMF (600 μL) were put in a 5 mL test tube, and $K_2CO_3$ (12 mg, 90 μmol) and benzyl bromide (7.8 μL, 11 mg, 66 μmol) were added. After stirred at 50° C. for 2 hours, an obtained mixture was cooled to room temperature. The mixture was extracted with diethyl ether (3x3 mL), and an extract was washed with saturated brine and dried with anhydrous sodium sulfate. An extraction liquid was concentrated under reduced pressure, and a residue was purified by the silica gel column chromatography {hexane/acetone=100:1} to obtain a compound 4c (16.8 mg, 42.8 μmol, 71%) as a yellow oil.

$^1H$ NMR (400 MHz, $CDCl_3$), 1.58 (s, 3H, $CH_3$), 1.59 (s, 3H, $CH_3$), 1.67 (s, 3H, $CH_3$), 1.84 (s, 3H, $CH_3$), 1.90-2.20 (m, 8H, $4CH_2$), 2.34 (s, 3H, $CH_3$), 5.02-5.14 (m, 2H, 2C═CH), 5.15 (s, 2H, $CH_2$), 5.79 (s, 1H, C═CH), 5.95 (d, J=11.2 Hz, 1H, C═CH), 6.16 (d, J=15.2 Hz, 1H, C═CH), 6.89 (dd, J=15.2, 11.2 Hz, 1H, C═CH), 7.26-7.42 (m, 5H, $C_6H_5$); $^{13}C$ NMR (100 MHz, $CDCl_3$), 14.01, 16.11, 17.27, 17.77, 25.78, 26.49, 26.77, 39.76, 40.33, 65.61, 117.63, 123.60, 124.34, 125.01, 128.12, 128.23 (2C), 128.59 (2C), 131.42 (2C), 133.40, 135.73, 136.57, 144.30, 153.89, 167.05; HR-MS (EI+, 100% acetone): m/z: calcd for $C_{27}H_{36}O_2(M^+)$ 392.2715; found, 392.2734.

Organotin compounds 15a, 15b, and 15c were synthesized by the following synthesis route.

[Chemical formula 11]

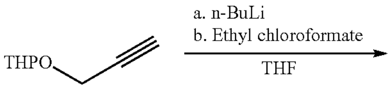

6

-continued

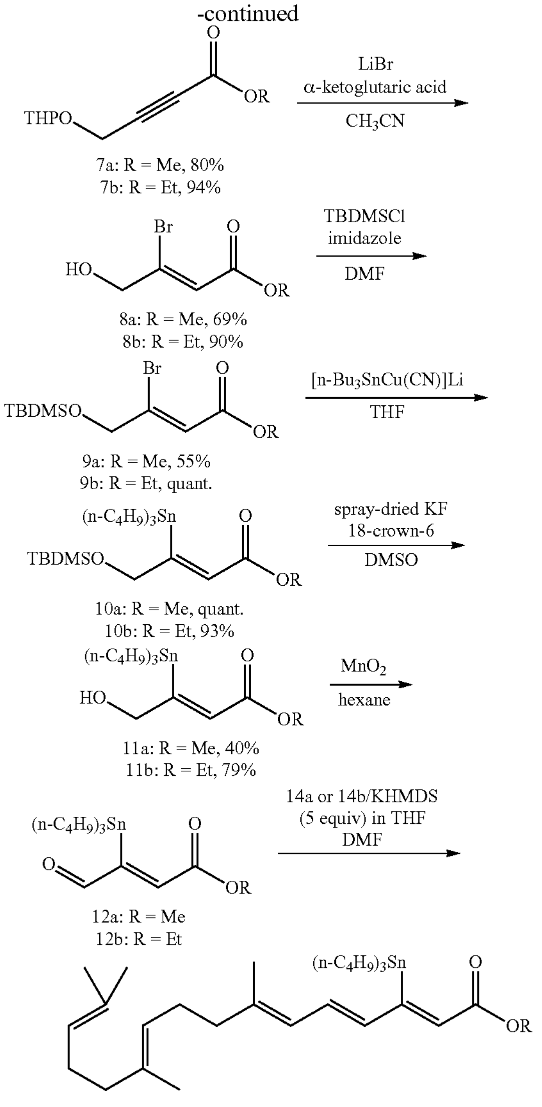

15a: R = Me, 39% (2 steps)
15b: R = Et, 17% (2 steps)

Synthesis of (Z)-4-(tert-butyl-dimethylsilyloxy)-3-bromo-2-butenoic acid ethyl ester 9b An (2Z)-3-bromo-4-hydroxy-2-butenoic acid ethyl ester (8b) was synthesized according to the procedure of a known document (M. Shengming, L. Xiyan, Org. Synth. 1995, 72, 112-115). 5a (1.56 g, 7.46 mmol) and dry DMF (10 mL) were put in a 250 mL round-bottom flask and cooled to 0° C., and imidazole (663 mg, 9.75 mmol) and tert-butyldimethylsilyl chloride (1.24 g, 8.25 mmol) were added. After stirred at room temperature for 4 hours, a reaction mixture was quenched with water (10 mL) and extracted with diethyl ether (3x10 mL). An organic layer was washed with water (30 mL) and dried with anhydrous sodium sulfate, and then a solvent was evaporated under reduced pressure. A crude product was subjected to the silica gel column chromatography {hexane/ethyl acetate=10:1} to obtain a compound 9b (2.40 g, 7.41 mmol, 99%) as a yellow oil.

$^1H$ NMR (400 MHz, $CDCl_3$), 0.10 (s, 6H, $2CH_3$), 0.92 (s, 9H, $3CH_3$), 1.30 (t, J=7.2 Hz, 3H, $CH_3$), 4.22 (q, J=7.2 Hz,

2H, $CH_2$), 4.29 (d, J=2.4 Hz, 2H, $CH_2$), 6.69 (t, J=2.4 Hz, 1H, C═CH); $^{13}$C NMR (100 MHz, $CDCl_3$), −5.38 (2C), 14.30, 18.38, 25.84 (3C), 60.66, 68.50, 117.16, 139.42, 164.59; HR-MS (EI+, 100% acetone): m/z: calcd for $C_8H_{14}{}^{79}BrO_3Si$ ([M-$C_4H_9$]$^+$) 264.9896; found, 264.9905.

Synthesis of (Z)-4-(tert-butyl-dimethylsilyloxy)-3-(tributylstannyl)-2-butenoic acid ethyl ester 10b Copper cyanide (537 mg, 6 mmol) and dry THF (10 mL) were put in a 50 mL two-neck round-bottom flask, an n-butyllithium solution (1.89 M hexane solution, 3.17 mL, 6.00 mmol) was dropped at −78° C., and a mixture was stirred for 15 minutes. Bis(tributyltin) (3.03 mL, 6.00 mmol) was dropped into the mixture at −78° C. After the mixture was stirred at 0° C. for 1 hour, a solution of bromide 9b (646 mg, 2.00 mmol) in dry THF (10 mL) was added to an obtained mixture of copper ate complexes at −78° C., and the mixture was stirred for 30 minutes. The mixture was quenched with brine, $NH_4Cl$ aq (10 mL), and 28% $NH_4OH$ at −78° C. An obtained mixture was extracted with diethyl ether (3×10 mL), and an extract was washed with water (30 mL) and dried with anhydrous sodium sulfate. A solvent was evaporated under reduced pressure. A crude product was subjected to the silica gel column chromatography {hexane/ethyl acetate=150:1} to obtain a compound 10b (995 mg, 1.87 mmol, 94%) as a yellow oil.

$^1$H NMR (400 MHz, $CDCl_3$), 0.07 (s, 6H, $2CH_3$), 0.86 (t, J=7.2 Hz, 9H, $3CH_3$), 0.90-0.98 (m, 6H, $3CH_2$), 0.92 (s, 9H, $3CH_3$), 1.20-1.34 (m, 9H, $3CH_2$ and $CH_3$), 1.35-1.51 (m, 6H, $3CH_2$), 4.18 (q, J=7.2 Hz, 2H, $CH_2$), 4.26-2.26 (m, 2H, $CH_2$), 6.56-6.82 (m, 1H, C═CH); $^{13}$C NMR (100 MHz, $CDCl_3$),−5.32 (2C), 10.89 (3C), 13.81 (3C), 14.43, 18.61, 26.05 (3C), 27.48 (3C), 29.29 (3C), 60.32, 68.70, 124.70, 168.40, 171.93; HR-MS (EI+, 100% acetone): m/z: calcd for $C_{20}H_{41}O_3Si^{120}Sn$ ([M-$C_4H_9$]$^+$) 477.1847; found, 477.1824.

Synthesis of (Z)-4-hydroxy-3-(tributylstannyl)-2-butenoic acid ethyl ester (11b)

10b (687 mg, 1.29 mmol) and dry DMSO (4 mL) were put in a 50 Ml round-bottom flask, and 18-crown-6-ether (1.03 g, 3.90 mmol) and potassium fluoride (226 mg, 3.89 mmol) were added at 0° C. After a mixture was stirred at room temperature for 3.5 hours, a phosphate buffer (pH 7.4) was added at 0° C., the mixture was extracted with diethyl ether (3×10 mL), an extract was washed with water (30 mL) and dried with anhydrous sodium sulfate, and a solvent was evaporated under reduced pressure. A crude product was separated by the silica gel column chromatography {hexane/ethyl acetate=15:1} to obtain a compound 11b (425 mg, 1.01 mmol, 78%) as a yellow oil.

$^1$H NMR (400 MHz, $CDCl_3$), 0.86 (t, J=7.2 Hz, 9H, $3CH_3$), 0.90-1.07 (m, 6H, $3CH_2$), 1.20-1.34 (m, 9H, $3CH_2$ and $CH_3$), 1.34-1.54 (m, 6H, $3CH_2$), 1.61 (t, J=6.0 Hz, 1H, OH), 4.18 (q, J=7.2 Hz, 2H, $CH_2$), 4.44-4.49 (m, 2H, $CH_2$), 6.53-6.80 (m, 1H, C═CH); $^{13}$C NMR (100 MHz, $CDCl_3$), 10.97 (3C), 13.79 (3C), 14.40, 27.48 (3C), 29.25 (3C), 60.47, 68.56, 124.77, 168.06, 172.25; HR-MS (EI+, 100% acetone): m/z: calcd for $C_{14}H_{27}O_3{}^{120}Sn$ ([M-$C_4H_9$]$^+$) 363.0982; found, 363.1002.

Synthesis of (2E,4E,6E,10E)-7,11,15-trimethyl-3-(tributylstannyl)-2,4,6,10,14-hexadecapentaenoic acid ethyl ester (15b)

11b (168 mg, 0.401 mmol) and hexane (3 mL) were put in a 20 mL round bottom of a flask. MnO 2 (1.04 g, 12.0 mmol) was added to a solution. An obtained suspension was stirred at 40° C. for 1.5 hours and then passed through a pad of Celite. When a filtrate was evaporated, a (Z)-4-oxo-3-(tributylstannyl)-2-butenoic acid ethyl ester (12b) was obtained as a yellow oil. 12b was used without further purification. 1 (137 mg, 0.328 mmol) and dry THF (2 mL) were put in a 30 mL two-neck round bottom of a flask. The solution was cooled to −78° C. in a dry ice/acetone bath, and bis(trimethylsilyl) amide potassium (1.0 M THF solution, 400 μL, 0.4 mmol) was added at this temperature. A reaction mixture was stirred for 1 hour, and 12b dissolved in THF (2 mL) was dropped at −78° C. After stirred at RT for 1 hour, an obtained mixture was cooled to 0° C., a phosphate buffer (pH 7.4) was added, and the mixture was extracted with diethyl ether (3×5 mL). An organic layer was washed with water (10 mL) and dried with anhydrous sodium sulfate. A solvent was evaporated under reduced pressure. A crude product was subjected to the silica gel column chromatography (hexane only) to obtain a compound 15b (18.6 mg, 30.7 μmol, 7.7%) as a yellow oil.

$^1$H NMR (400 MHz, $CDCl_3$), 0.86 (t, J=7.4 Hz, 9H, $3CH_3$), 0.91-1.12 (m, 6H, $3CH_2$), 1.20-1.35 (m, 9H, $3CH_2$, $CH_3$), 1.35-1.57 (m, 6H, $3CH_2$), 1.59 (s, 3H, $CH_3$), 1.60 (s, 3H, $CH_3$), 1.67 (s, 3H, $CH_3$), 1.82 (s, 3H, $CH_3$), 1.90-2.20 (m, 8H, $4CH_2$), 4.17 (q, J=7.4 Hz, 2H, $CH_2$), 5.00-5.20 (m, 2H, 2C═CH), 5.92 (d, J=10.8 Hz, 1H, C═CH), 6.44 (d, J=15.6 Hz, 1H, C═CH), 6.46 (s, 1H, C═CH), 6.71 (dd, J=15.6, 11.4 Hz, 1H, C═CH); $^{13}$C NMR (100 MHz, $CDCl_3$), 12.43 (3C), 13.79 (3C), 14.46, 16.10, 17.24, 17.77, 25.78, 26.57, 26.79, 27.48 (3C), 29.21 (3C), 39.78, 40.29, 60.30, 123.74, 124.39, 125.44, 127.73, 131.43, 132.36, 135.62, 136.21, 142.94, 168.33, 168.42; HR-MS (EI+, 100% acetone): m/z: calcd for $C_{29}H_{49}O_2{}^{120}Sn$ ([M-$C_4H_9$]$^+$) 549.2755; found, 549.2747.

Synthesis of (2E,4E,6E,10E)-7,11,15-trimethyl-3-(tributylstannyl)-2,4,6,10,16-hexadecapentaenoic acid methyl ester 15a and ethyl ester 15b 15a was synthesized from a (2E,6E)-3,7,11-trimethyl-2,6,10-(dodecatrienyl) phosphonic acid dimethyl ester (14a) (11.7 mg, 37.2 μmol) and (Z)-4-oxo-(13.8 mg, 34.2 μmol) (7.9 mg, 13.4 μmol, 39%). In addition, from a 3-(tributylstannyl)-2-butenoic acid methyl ester ((Z)-4-hydroxy-3-(tributylstannyl)-2-butenoic acid methyl ester (127 mg, 0.313 mmol), 15b as a yellow oil was obtained by a similar procedure (10.0 mg, 17.0 μmol, 15%).

$^1$H NMR (400 MHz, $CDCl_3$), 0.86 (t, J=7.4 Hz, 9H, $3CH_3$), 0.93-1.10 (m, 6H, $3CH_2$), 1.24-1.33 (m, 6H, $3CH_2$), 1.42-1.51 (m, 6H, $3CH_2$), 1.585 (s, 3H, $CH_3$), 1.594 (s, 3H, $CH_3$), 1.67 (s, 3H, $CH_3$), 1.82 (s, 3H, $CH_3$), 1.93-2.26 (m, 8H, $4CH_2$), 3.72 (s, 3H, $CH_3$), 5.06-5.10 (m, 2H, 2C═CH), 5.92 (d, J=10.8 Hz, 1H, C═CH), 6.44 (d, J=15.6 Hz, 1H, C═CH), 6.46 (s, 1H, C═CH), 6.71 (dd, J=15.6, 11.4 Hz, 1H, C═CH); $^{13}$C NMR (100 MHz, $CDCl_3$), 12.40 (3C), 13.81 (3C), 16.10, 17.26, 17.77, 25.80, 26.55, 26.79, 27.48 (3C), 29.21 (3C), 39.80, 40.29, 51.56, 123.72, 124.37, 125.42, 127.33, 131.43, 132.51, 135.64, 136.23, 143.13, 168.67, 168.78; HR-MS (EI+, 100% acetone): m/z: calcd for $C_{28}H_{47}O_3{}^{120}Sn$ ([M-$C_4H_9$]$^+$) 535.2598; found, 535.2603.

Synthesis of (2E,4E,6E,10E)-7,11,15-trimethyl-3-(tributylstannyl)-2,4,6,10,14-hexadecapentaenoic acid 16

A mixture of 15a and 15b (1:1 molar ratio, 22.7 mg, 38.4 μmol), methanol (200 μL), and 2-propanol (200 μL) were put in a 5 mL test tube. After addition of 10 M KOH in $CH_3OH$/H2O (2:1, v/v), 100 μL, 1.00 mmol, a reaction mixture was stirred at 100° C. for 30 minutes. After neutralization with a formic acid (1 mL), an obtained mixture was extracted with diethyl ether (3×3 mL), and an extract was washed with a brain (10 mL) and dried with anhydrous sodium sulfate. A solvent was evaporated under reduced pressure. A crude product was subjected to the silica gel column chromatography {hexane/ethyl acetate=10:1} to obtain a yellow oil (15.6 mg, 27.0 μmol, 71%).

$^1$H NMR (400 MHz, $CDCl_3$), 0.86 (t, J=7.4 Hz, 9H, $3CH_3$), 0.91-1.12 (m, 6H, $3CH_2$), 1.20-1.35 (m, 6H, $3CH_2$), 1.35-1.54 (m, 6H, $3CH_2$), 1.59 (s, 3H, $CH_3$), 1.60 (s, 3H, $CH_3$), 1.67 (s, 3H, $CH_3$), 1.83 (s, 3H, $CH_3$), 1.90-2.20 (m, 8H, $4CH_2$), 5.02-5.20 (m, 2H, 2C═CH), 5.93 (d, J=11.6 Hz, 1H, C═CH), 6.47 (d, J=16.0 Hz, 1H, C═CH), 6.50 (s, 1H, C═CH), 6.71 (dd, J=16.0, 11.6 Hz, 1H, C═CH), 8.82-9.78 (br s, 1H, COOH).

Synthesis of (2E,4E,6E,10E)-7,11,15-trimethyl-3-(tributylstannyl)-2,4,6,10,14-hexadecapentaenoic acid benzyl ester 15c An (2E,4E,6E,10E)-7,11,15-trimethyl-3-(tributylstannyl)-2,4,6,10,14-hexadecapentaenoic acid (15.6 mg, 27.0 μmol) and dry DMF (200 μL) in a 5 mL test tube. $K_2CO_3$ (5.60 mg, 40.5 μmol) and benzyl bromide (3.50 μL, 5.08 mg, 29.7 μmol) were added to a solution. After stirred at 50° C. for 1 hour, an obtained mixture was cooled to room temperature. The mixture was extracted with diethyl ether (3×3 mL), and an extract was washed with brine (10 mL) and dried with anhydrous sodium sulfate. The solution was concentrated under reduced pressure, and a residue was purified by the silica gel column chromatography {hexane/acetone=100:1} to obtain a compound 15c (13.5 mg, 20.2 μmol, 75%) as a yellow oil.

$^1$H NMR (400 MHz, $CDCl_3$), 0.86 (t, J=7.6 Hz, 9H, $3CH_3$), 0.91-1.12 (m, 6H, $3CH_2$), 1.20-1.35 (m, 6H, $3CH_2$), 1.35-1.54 (m, 6H, $3CH_2$), 1.58 (s, 3H, $CH_3$), 1.59 (d, J=0.8 Hz, 3H, $CH_3$), 1.66 (s, 3H, $CH_3$), 1.81 (s, 3H, $CH_3$), 1.90-2.19 (m, 8H, $4CH_2$), 5.02-5.14 (m, 2H, 2C═CH), 5.17 (s, 2H, $CH_2$), 5.91 (d, J=11.6 Hz, 1H, C═CH), 6.44 (d, J=15.2 Hz, 1H, C═CH), 6.52 (s, 1H, C═CH), 6.72 (dd, J=15.2, 11.6 Hz, 1H, C═CH), 7.27-7.42 (m, 5H, $C_6H_5$); $^{13}$C NMR (100 MHz, $CDCl_3$), 12.45 (3C), 13.83 (3C), 16.10, 17.28, 17.77, 22.80, 26.55, 26.79, 27.50 (3C), 29.22 (3C), 39.80, 40.31, 66.10, 123.72, 124.37, 125.44, 127.29, 128.18, 128.32 (2C), 128.59 (2C), 131.43, 132.63, 135.64, 136.16, 136.38, 143.25, 168.23, 169.37; HR-MS (EI+, 100% acetone): m/z: calcd for $C_{34}H_{51}O_2{}^{120}Sn$ ($[M-C_4H_9]^+$) 611.2911; found, 611.2915.

The [$^{11}$C]-4a, [$^{11}$C]-4b, [$^{11}$C]-4c, and [$^{11}$C]-3 were synthesized by the following synthesis method.

[Chemical formula 12]

(a)

15a-c 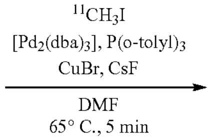

-continued

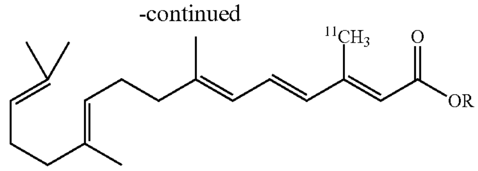

[$^{11}$C]-4a-c (b)

[$^{11}$C]-4a 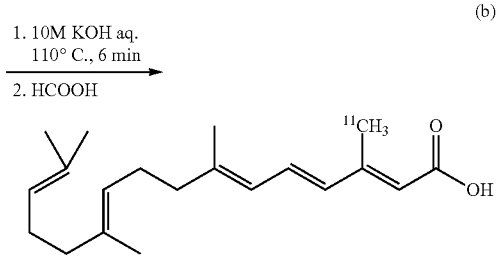

[$^{11}$C]-3

Synthesis of (2E,4E,6E,10E)-3,7,11,15-tetramethyl-2,4,6,10,14-hexadecapentaenoic acid ethyl ester 4b by C-methylation using nonradioactive methyl iodide $[Pd_2(dba)_3]$ (11.5 mg, 12.6 μmol), P(o-tolyl)3 (27.7 mg, 91.1 μmol), CuBr (6.50 mg, 45.3 μmol), and CsF (17.3 mg, 114 μmol) were put in a 1 mL Schlenk flask with argon substitution. A DMF (2 mL) solution of a stannyl precursor 15b (13.3 mg, 22.0 μmol) was transferred to the Schlenk flask through a stainless steel cannula at −10° C., after addition of methyl iodide (220 μL, 0.10 M in DMF, 22 μmol), a mixture was heated at 60° C. for 1 hour, and then an obtained mixture was quenched with water and extracted with diethyl ether (3×3 mL). Extracted organic layers were combined, washed with water and saturated brine, dried with anhydrous sodium sulfate, filtered, and concentrated. A crude product was separated by the silica gel column chromatography {hexane/ethyl acetate=100:1} to obtain the acyclic retinoid 4b as a light yellow oil (5.80 mg, 17.5 μmol, 80%).

$^1$H NMR (400 MHz, $CDCl_3$), 1.27 (t, J=7.2 Hz, 3H, $CH_3$), 1.58 (s, 3H, $CH_3$), 1.59 (d, J=0.8 Hz, 3H, $CH_3$), 1.66 (d, J=0.8 Hz, 3H, $CH_3$), 1.84 (d, J=0.8 Hz, 3H, $CH_3$), 1.90-2.20 (m, 8H, $4CH_2$), 2.32 (d, J=0.8 Hz, 3H, $CH_3$), 4.15 (q, J=7.2 Hz, 2H, $CH_2$), 5.00-5.17 (m, 2H, 2C═CH), 5.73 (s, 1H, C═CH), 5.95 (d, J=11.2 Hz, 1H, C═CH), 6.16 (d, J=15.6 Hz, 1H, C═CH), 6.83 (dd, J=15.6, 11.2 Hz, 1H, C═CH).

Synthesis of [$^{11}$C] 4c by Rapid C-[$^{11}$C] methylation Using Radioactive methyl iodide $[Pd_2(dba)_3]$ (1.0 mg, 1.1 μmol), P(o-tolyl)3 (2.4 mg, 8 μmol), CuBr (0.6 mg, 4 μmol), CsF (1.5 mg, 10 μmol), and a stannyl precursor 15c (1.1 mg, 1.6 μmol) in DMF (400 μL) were maintained below −10° C. by cooling while waiting for preparation of [$^{11}$C] $CH_3I$. [$^{11}$C] $CH_3I$ formed from [$^{11}$C] $CO_2$ using the conventional $LiAlH_4$ method was trapped in a reaction mixture, the cooling was stopped, and then the mixture was rapidly heated to 65° C. and bubbled after left for 2 minutes. For 2 minutes with a $N_2$ gas. To avoid bumping, the reaction mixture was cooled for 10 seconds. After dilution with $CH_3CN$ (600 μL), the mixture was passed through a fine filter F (F162, Forte Grow Medical co., ltd.) with quartz glass wool (Tosho co., ltd.), and preparative HPLC (mobile phase, $CH_3CN$ only, column, CAPCELL PAK C18 UG 120 5 μm, 10 mm (inner diameter)×250 mm, flow rate, 5 mL/min, UV detection, 280 nm, retention time, 7.37 to 8.31 minutes). An HPLC analysis yield was calculated at 97% from a radio-HPLC peak area of the reaction mixture. Desired fractions were collected in a flask, and an organic solvent was removed under reduced pressure. A desired radioactive tracer was dissolved in a 0.25% solution of polysorbate 80 in saline (3.0 mL). Total synthesis time including purification by HPLC and preparation of radiopharmaceutical formulation for intravenous administration was 31 minutes. Separated radioactivity was 2.87 GBq at an end of synthesis, and specific radioactivity was 144 GBq $\mu mol^{-1}$. A decay-corrected radiochemical yield was 57%, which was calculated based on radioactivity of $[^{11}C]CH_3I$ trapped in the solution. Identification of $[^{11}C]$4c was confirmed by co-injection with a real sample of non-radiolabeled 4c by analytical HPLC (mobile phase, $CH_3CN$ only, column, CAPCELL PAK C 18, 4.6 mm (id)×250 mm, flow rate, 1 mL/min; UV detection, 280 nm; retention time, 8.0 minutes). Chemical and radiochemical purities analyzed at 280 nm were >99% and >97%, respectively.

Synthesis of $[^{11}C]$-3 by rapid $[^{11}C]$ methylation using radioactive methyl iodide $[Pd_2(dba)_3]$ (1.0 mg, 1.1 μmol), P(o-tolyl)3 (2.4 mg, 8 μmol), CuBr (0.6 mg, 4 μmol), CsF (1.5 mg, 10 μmol), and a stannyl precursor 15a (0.9 mg, 1.5 μmol) in DMF (300 μL) were maintained below −10° C. by cooling while waiting for preparation of $[^{11}C]$ $CH_3I$. $[^{11}C]$ $CH_3I$ formed from $[^{11}C]$ $CO_2$ using the conventional $LiAlH_4$ method was trapped in a reaction mixture, the cooling was stopped, and then the mixture was rapidly heated to 65° C. and bubbled after left for 2 minutes. For 2 minutes with a $N_2$ gas. To avoid bumping, the reaction mixture was cooled for 10 seconds. After an 8M KOHaq. (500 μL) solution was added to the mixture, the $N_2$ gas was bubbled at 100° C. for 6 minutes. After cooling for 10 seconds, the reaction mixture was diluted with $CH_3CN/CH_3CN/H_2O$ (60:36:4 v/v/v, 1 mL) containing sodium ascorbate (2.2 mg, 11 μmol), the fine filter F (F162, Forte Grow Medical co., ltd.) and quartz glass wool (Tosoh co., ltd.) were used for the mixture, and preparative HPLC (mobile phase, $CH_3CN$/0.2% HCOOH in water=90:10; column), CAPCELL PAK C18 UG 120 5 μm, 10 (id)×250 mm, flow rate, 5 mL/min, UV detection, 280 nm, retention time, 8:45 to 9:32 minutes). An HPLC analysis yield (%) was determined from a radio-HPLC peak area of the reaction mixture. Desired fractions were collected in a flask, and an organic solvent was removed under reduced pressure. A desired radioactive tracer was dissolved in a 0.25% solution of polysorbate 80 in saline (3.0 mL). Total synthesis time including HPLC purification and preparation of radiopharmaceutical formulation for intravenous administration was 40 minutes. Separated radioactivity was 0.94 GBq at an end of synthesis, and specific radioactivity was 186 GBq $\mu mol^{-1}$. A decay-corrected radiochemical yield was 25%, which was calculated based on radioactivity of $[^{11}C]CH_3I$ trapped in the solution. Chemical identity of $[^{11}C]$ 3 was confirmed by co-injection with a sample of non-radiolabeled 3 by analytical HPLC (mobile phase, $CH_3CN$/0.2% HCOOH aqueous solution=90:10, column, CAPCELL PAK C18, 4.6 (id)×250 mm, flow rate, 1 mL/min, UV detection, 280 nm, retention time, 7.7 min). Chemical and radiochemical purities analyzed at 280 nm were 83% and 99%, respectively.

Radioactivity, molar activity of radioactivity, and decay-corrected radiochemical yield of the $[^{11}C]$-4a, $[^{11}C]$-4b, $[^{11}C]$-4 c, and $[^{11}C]$-3 synthesized as described above are shown in Table 1. From this table, it is found that the $[^{11}C]$-4a, $[^{11}C]$-4b, $[^{11}C]$-4c, and $[^{11}C]$-3 have sufficient radioactivity for a PET probe.

TABLE 1

| Compound | Radioactivity [GBq] | Molar activity [GBq $\mu mol^{-1}$] | DCY [%] |
|---|---|---|---|
| $[^{11}C]$-4a | 4.33 | 157 | 82 |
| $[^{11}C]$-4b | 3.15 | 134 | 66 |
| $[^{11}C]$-4c | 2.87 | 144 | 57 |
| $[^{11}C]$-3 | 0.94 | 186 | 25 |

Synthesis of peretinoin 3

The peretinoin 3, which was not labeled with $^{11}C$, was synthesized from phosphate 14a, which served as a precursor when the $[^{11}C]$-3 was synthesized, by applying the Horner-Wadsworth-Emmons (HWE) reaction, which allows formation of olefins that are highly selective about an E-body.

First, trans, trans-farnesol 16 was converted into a chloride 17 (a yield of 51%), and then the phosphate 14a was synthesized in a yield of 64% by the Michaelis-Albuzov reaction using trimethyl phosphite.

[Chemical formula 13]

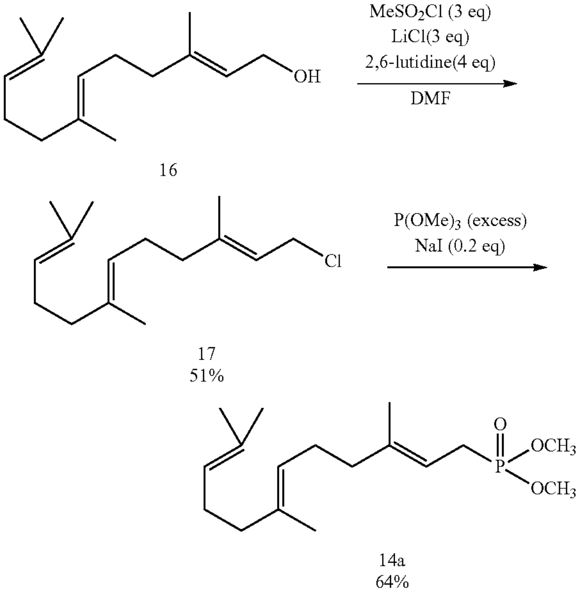

16

17
51%

14a
64%

On the other hand, an aldehyde form 20, which was another compound for target acyclic retinoid synthesis, was synthesized as follows. In other words, a hydroxy ester 19 of an E isomer was synthesized at a yield of 57% by the Wittig olefin synthesis using hydroxyacetone 18 as a starting material, and the aldehyde form 20 maintaining the E configuration was synthesized at a yield of 43% by oxidation using manganese dioxide.

[Chemical formula 14]

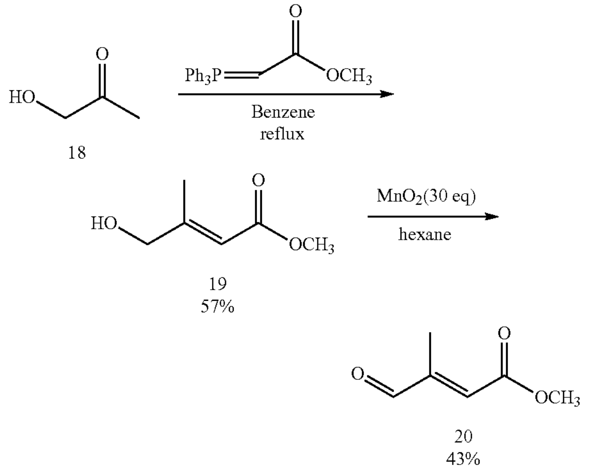

18

19
57%

20
43%

The phosphate 14a and the aldehyde 20 synthesized by the synthesis methods described above were bonded with a carbon-carbon double bond by the HWE reaction to obtain the peretinoin 3. In other words, potassium hexamethyldisilazide (KHMDS) was selected as a base for adjusting ylide from 14a, a methyl ester form 4a of 4,5-didehydro GGA (the peretinoin) was synthesized under a condition of 14a/KHMDS/14 (1:1:1 molar ratio), and this was hydrolyzed with a strong base to synthesize the target peretinoin 3 in three steps at a yield of 26%.

[Chemical formula 15]

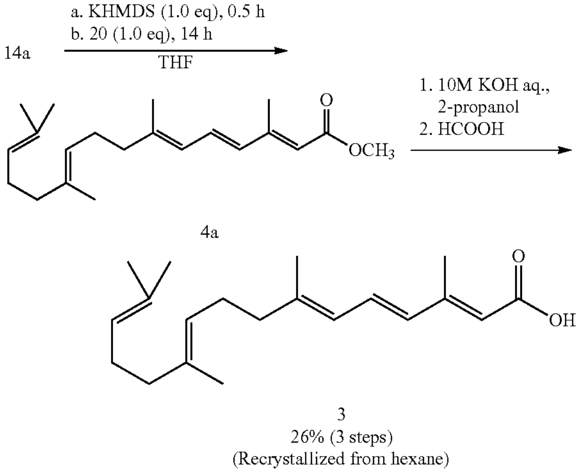

14a

4a 3
26% (3 steps)
(Recrystallized from hexane)

The procedure of synthesis and analytical data of the peretinoin 3 are described in detail below.

(2E,6E)-1-Chloro-3,7,11-trimethyldodeca-2,6,10-triene (17)

$^{1}H$ NMR (400 MHz, $CDCl_3$): δ=1.60 (s, 6H, $2CH_3$), 1.68 (s, 3H $CH_3$), 1.73 (s, 3H, $CH_3$), 1.98-2.11 (m, 8H, $4CH_2$), 4.10 (d, J=7.6 Hz, $CH_2$), 5.06-5.14 (m, 2H, olefine), 5.45 (t, J=7.6 Hz, olefine).

Dimethyl ((2E,6E)-3,7,11-trimethyldodeca-2,6,10-trien-1-yl)phosphonate (14a)

$^{1}H$ NMR (400 MHz, $CDCl_3$): δ=1.60 (s, 6H, $2CH_3$), 1.66 (s, 3H, $CH_3$), 1.69 (s, 3H, $CH_3$), 1.95-2.10 (m, 8H, $4CH_2$), 2.58 (dd, J=22.0, 7.6 Hz, $CH_2$), 3.74 (d, J=10.4 Hz, 6H, $2CH_3O$), 5.08-5.20 (m, 3H, olefines); $^{13}C$ NMR (100 MHz, $CDCl_3$) δ=16.00, 16.26 (d, $J_{P-C}$=1.9 Hz) 17.67, 25.45 (d, $J_{P-C}$=139.2 Hz), 25.69 (2C), 26.35 (d, $J_{P-C}$=3.8 Hz), 26.70, 39.69, 52.57 (d, $J_{P-C}$=6.7 Hz, 2C), 111.98 (d, $J_{P-C}$=10.5 Hz), 123.72, 124.28, 131.32, 135.32, 140.57 (d, $J_{P-C}$=14.3 Hz).

Methyl (E)-4-hydroxy-3-methylbut-2-enoate (19)

Hydroxyacetone (6.16 mL, 6.65 g, 89.8 mmol), benzene (90 mL), and methyl (triphenylphosphoranylidene) acetate (30.0 g, 89.8 mmol) were added to a 300-mL recovery flask at room temperature in order, and heated and refluxed for 24 hours. After concentration under reduced pressure, an obtained residue was purified by the silica gel column chromatography (hexane/ethyl acetate=3/1) to obtain a yellow oily target product 19 (6.63 g, 51.0 mmol, 57%).

$^{1}H$ NMR (400 MHz, $CDCl_3$): δ=2.10 (s, 3H, $CH_3$), 3.72 (s, 3H, $CH_3$), 4.15-4.16 (m, 2H, $CH_2$), 5.99-6.01 (m, 1H, olefine); $^{13}C$ NMR (100 MHz, $CDCl_3$): δ=15.60, 51.01, 67.04, 113.24, 157.50 167.19.

Methyl (E)-3-methyl-4-oxobut-2-enoate (20)

13 (6.45 g, 49.6 mmol) was added to a 1-L recovery flask and dissolved in hexane (500 mL), then manganese dioxide (129 g, 1.48 mol) was added, and a mixture was stirred at room temperature for 1 hour. Thereafter, an oxidant was removed by Celite filtration, a filtrate was concentrated under reduced pressure, and then an obtained residue was purified by the silica gel column chromatography (hexane/ethyl acetate=3/1) to obtain a yellow oily target product 20 (2.75 g, 21.5 mmol, 43%).

$^{1}H$ NMR (400 MHz, $CDCl_3$): δ=2.18 (d, 1.2 Hz, 3H, $CH_3$), 3.84 (s, 3H, $CH_3$), 6.52 (t, 1.2 Hz, 1H, olefine), 9.57 (s, 1H, CHO); $^{13}C$ NMR (100 MHz, $CDCl_3$): δ=10.85, 52.00, 135.00, 150.70, 165.92, 194.43.

(2E,4E,6E,10E)-3,7,11,15-tetramethylhexadeca-2,4,6,10,14-pentaenoic acid (3)

A THF (170 mL) solution of 14a (6.12 g, 19.5 mmol) was added to two 250-mL Schlenks under an argon atmosphere, and potassium hexamethyldisilazane (1.0 M THF solution, 19.5 mL, 19.5 mmol) was added at −78° C. After a mixture was stirred for 30 minutes, 20 (2.49 g, 19.5 mmol) dissolved in THF (30 mL) was added at −78° C., and then the mixture was stirred for 15 hours while the temperature was being gradually raised to room temperature. Then, under ice cooling, a saturated aqueous ammonium chloride solution (100 mL) was added, and the mixture was extracted with ethyl acetate (3×40 mL). Subsequently, an organic layer was washed with saturated saline (100 mL) and dried with anhydrous sodium sulfate. After concentration under reduced pressure, an obtained residue was purified by the silica gel column chromatography (hexane/ethyl acetate=50/1) to obtain a crude product (3.91 g).

The crude product (3.91 g) was added to a 100-mL recovery flask and dissolved in 2-propanol (24 mL), then a 10 M aqueous potassium hydroxide solution (40 mL) was added, and the mixture was heated and refluxed for 1.5 hours. Thereafter, a formic acid (32 mL) was added under ice cooling, and the mixture was concentrated under reduced pressure and then extracted with ethyl acetate (3×20 mL). Subsequently, the organic layer was washed with saturated saline (40 mL) and dried with anhydrous sodium sulfate. After concentration under reduced pressure, it was dissolved in hexane (8.7 ml) and crystallized at −20° C. A filtrate was concentrated and concentrated under reduced pressure, and then an obtained residue was purified by the silica gel column chromatography (hexane/ethyl acetate=10/1) and combined with a product by recrystallization to obtain the peretinoin 3 (1.50 g, 4.97 mmol, 26%, 3 steps) as a pale yellow needle-like crystal.

$^1$H NMR (400 MHz, $CDCl_3$): δ=1.60 (s, 3H, $CH_3$), 1.61 (s, 3H, $CH_3$), 1.68 (s, 3H, $CH_3$), 1.86 (s, 3H, $CH_3$), 1.98-2.16 (m, 8H, $2CH_2$), 2.34 (s, 3H, $CH_3$), 5.09-5.10 (m, 2H, olefines), 5.77 (s, 1H, olefine), 5.98 (d, J=10.8 Hz, 1H, olefine), 6.21 (d, J=14.8 Hz, 1H, olefine), 6.90 (dd, J=15.2, 10.8 Hz, 1H, olefine), 9.35-11.97 (br s, 1H, COOH).

<Pharmacokinetic Tests of 1'C-Labeled Acyclic Retinoid>

The $^{11}$C-labeled acyclic retinoid 4c and the $^{11}$C-labeled peretinoin 3 synthesized by the methods described above were administered intravenously (i.v.) to Sprague-Dawley rats and cynomolgus monkeys as a PET probe, and PET images were photographed.

In a Case where the 1C-Labeled Peretinoin 3 was Administered

Figure 2:
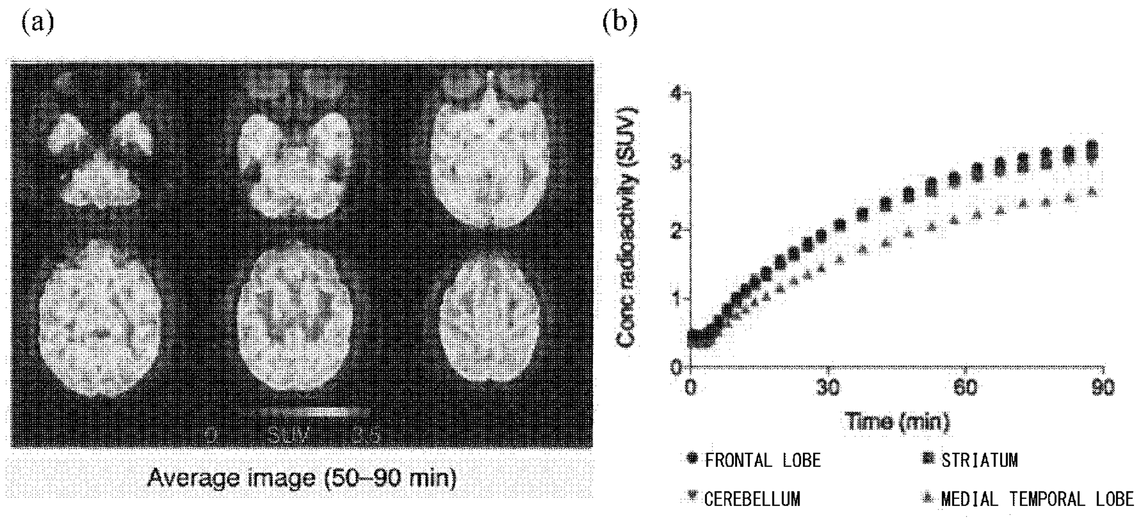
FIG. 2 is a PET image (a) and a graph (b) of radioactivity in a brain when the $^{11}C$-labeled peretinoin [$^{11}C$]-3 was administered to a cynomolgus monkey.

A PET image in a case where the $^{11}$C-labeled peretinoin 3 was administered to a rat is shown in FIG. 1(*a*), and a PET image in a case where the $^{11}$C-labeled peretinoin 3 was administered to a cynomolgus monkey is shown in FIG. 2(*a*). From these drawings, it was found that the $^{11}$C-labeled peretinoin 3 migrated into a brain in both the rat and the cynomolgus monkey. Further, from measurement of radioactivity intensity in the brain for each time shown in FIGS. 1(*b*) and 2(*b*), it was found that the $^{11}$C-labeled peretinoin 3 began to migrate into the brain within several minutes, and that the concentration in the brain continued to increase over time, and accumulated to 1.3 times in the rat and 3.0 times in the cynomolgus monkey as compared with the concentration when the $^{11}$C-labeled peretinoin 3 was uniformly distributed throughout a body. From the results of the pharmacokinetic tests described above, it was clarified that the $^{11}$C-labeled peretinoin 3 was a substance that rapidly permeated a blood-brain barrier and accumulated in the brain. From this, it was found that the $^{11}$C-labeled peretinoin 3 could be particularly suitably used as a PET probe for imaging in the brain.

In a Case where $^{11}$C-Labeled Acyclic Retinoid 4c was Administered

Figure 3:
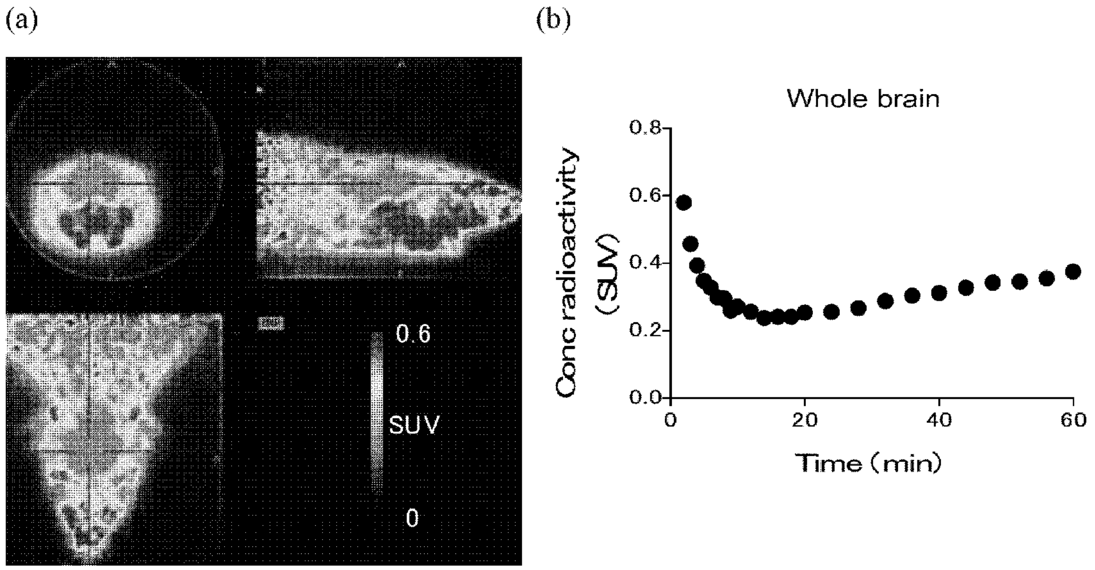
FIG. 3 is a PET image (a) and a graph (b) of radioactivity in a brain when a $^{11}C$-labeled acyclic retinoid [$^{11}C$]-4c was administered to a rat.
Figure 4:
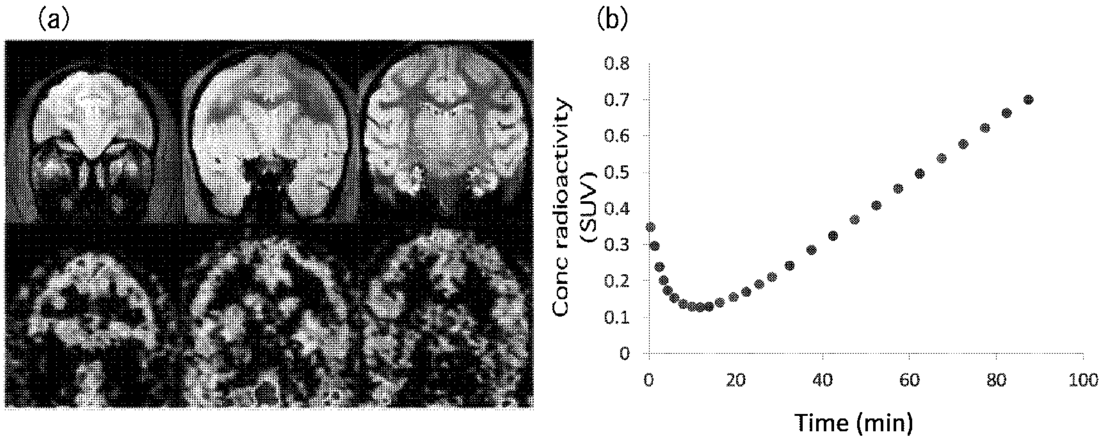
FIG. 4 is a PET image (a) and a graph (b) of radioactivity in a brain when the $^{11}C$-labeled acyclic retinoid [$^{11}C$]-4c was administered to a cynomolgus monkey.

A PET image in a case where the $^{11}$C-labeled acyclic retinoid 4c was administered to a rat is shown in FIG. 3(*a*), and a PET image in a case where the $^{11}$C-labeled acyclic retinoid 4c was administered to a cynomolgus monkey is shown in FIG. 4(*a*). It was found that the $^{11}$C-labeled acyclic retinoid 4c migrated into a brain in both animal species. From the above results, it was found that the $^{11}$C-labeled acyclic retinoid 4c could migrate into the brain, could be used as a PET probe, and could be used for imaging in the brain.

Further, from measurement of radioactivity in the brain for each time shown in FIGS. 3(*b*) and 4(*b*), it was found that the $^{11}$C-labeled acyclic retinoid 4c, which was a benzyl ester form, was less likely to migrate into the brain immediately after administration as compared with the $^{11}$C-labeled peretinoin 3, which was a free carboxylic acid, and that the migration into the brain started after 10 minutes or more. As a reason for this, it is presumed that the $^{11}$C-labeled acyclic retinoid 4c, which is a benzyl ester form, is metabolized to the $^{11}$C-labeled peretinoin 3, which is a free carboxylic acid, and then migrates into the brain.

In a Case where $^{11}$C-Labeled Acyclic Retinoid 4b was Administered

Figure 5:
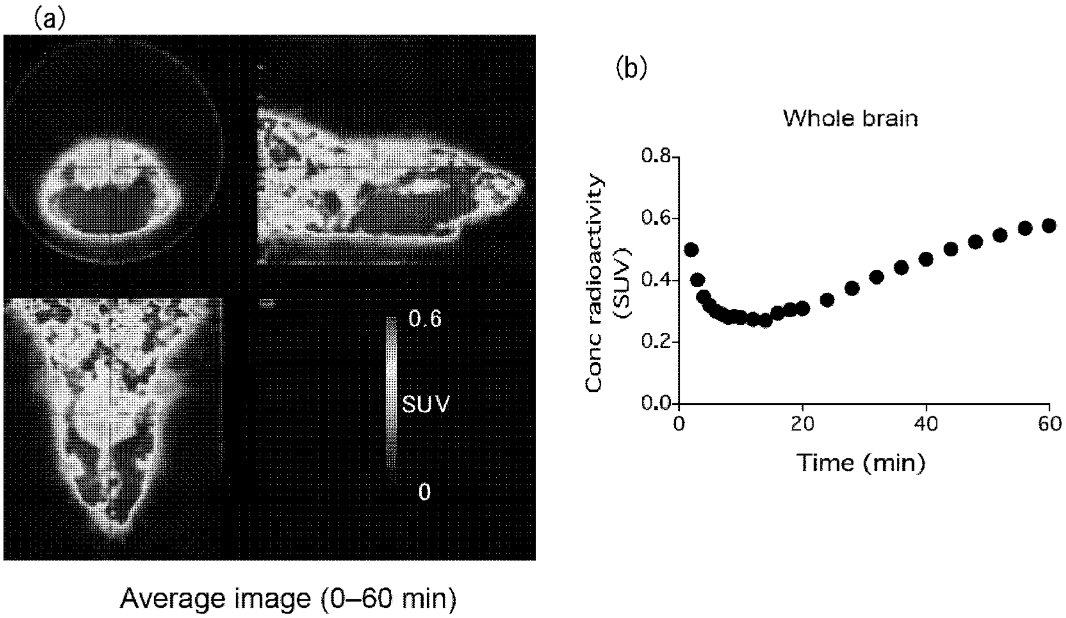
FIG. 5 is a PET image (a) and a graph (b) of radioactivity in a brain in a case where a $^{11}C$-labeled acyclic retinoid [$^{11}C$]-4b was administered to a rat.

A PET image in a case where the $^{11}$C-labeled acyclic retinoid 4b was administered to a rat is shown in FIG. 5*a*. From this image, it was found that the $^{11}$C-labeled acyclic retinoid 4b could migrate into the brain of the rat, was useful as a PET probe, and could be used for imaging in the brain. Further, from measurement of radioactivity in the brain shown in FIG. 5(*b*), it was found that the $^{11}$C-labeled acyclic retinoid 4b, which was an ethyl ester form, was less likely to migrate into the brain immediately after administration as compared with the $^{11}$C-labeled peretinoin 3, which was a free carboxylic acid, and that the migration into the brain started after 10 minutes or more. As a reason for this, it is presumed that the $^{11}$C-labeled acyclic retinoid 4b, which is an ethyl ester form, is metabolized to the $^{11}$C-labeled peretinoin 3, which is a free carboxylic acid, and then migrates into the brain.

<Functional Effect of Peretinoin 3>

The functional effect of peretinoin 3, an acyclic retinoid that is not labeled with $^{11}$C, was evaluated.

(Inhibitory Effect on Thrombin Toxicity)

Thrombin is known to induce cerebral cortex cell death and striatal tissue atrophy. Therefore, an experiment for evaluating thrombin toxicity was performed. In other words, a coronal section having a thickness of 300 μm was prepared from a brain of a Wistar/ST rat aged 2 to 3 days after birth, a fan-shaped tissue piece including a cerebral cortex and striatum was cut out, and then left to stand on a porous membrane (Millicell-CM, Millipore Corporation), and culture was maintained at a gas-liquid interface under a conditions of 34° C./5% $CO_2$ (medium composition: 50% minimal essential medium, 25% Hanks' balanced salt solution, 25% horse serum). On the 12th day of culture, the medium was replaced with a serum-free medium (medium composition: 75% minimal essential medium, 25% Hanks' balanced salt solution) containing 5 μg/ml propidium iodide (PI), drug treatment such as peretinoin was started, and thrombin (100 U/ml) was added to the medium 24 hours later. PI fluorescence images were acquired using a fluorescence microscope (Keyence) 72 hours after a start of thrombin treatment, and a degree of cell death was evaluated using fluorescence intensity of a cortical region as an index (sections of 100 μM NMDA treated for 72 hours were provided for each experiment, and their PI fluorescence intensity was standardized as 100%). Further, an area of a striatal region in each tissue piece was measured from bright field images of cultured tissue pieces acquired before and after the thrombin treatment, and a rate of tissue atrophy due to the thrombin treatment was quantified.

Results

Figure 6:
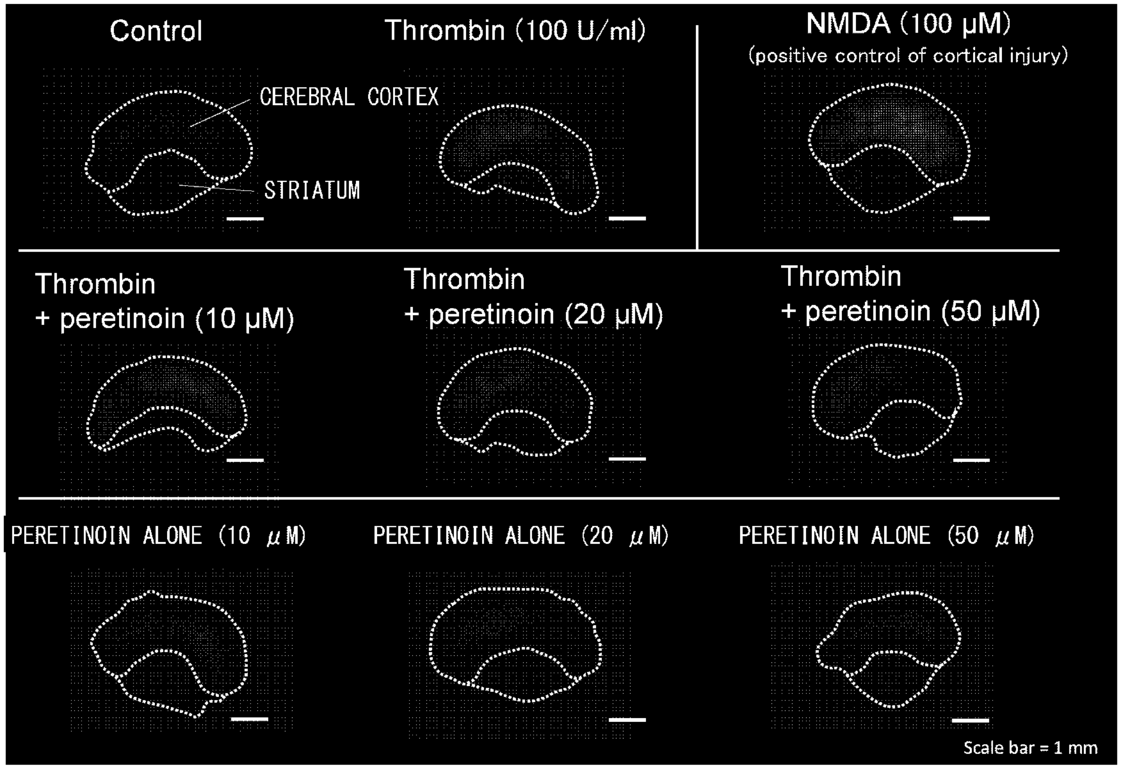
FIG. 6 is PI fluorescence images showing an inhibitory effect of peretinoin 3 on brain tissue disorders induced by thrombin.
Figure 7:
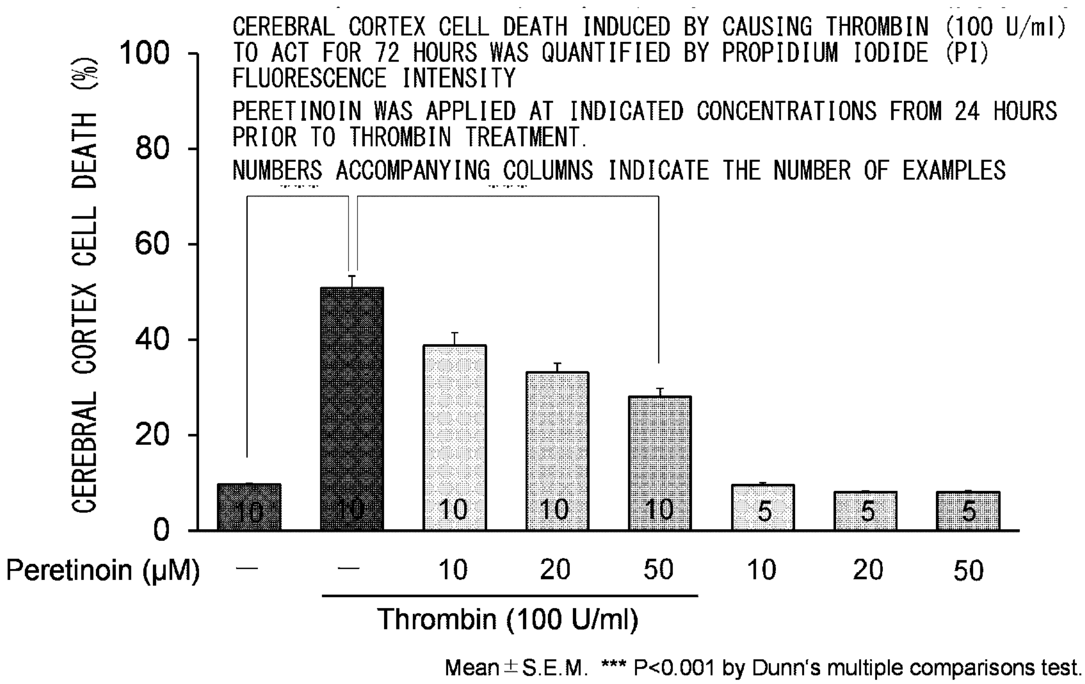
FIG. 7 is a graph showing a rate of cerebral cortex cell death induced by thrombin.
Figure 8:
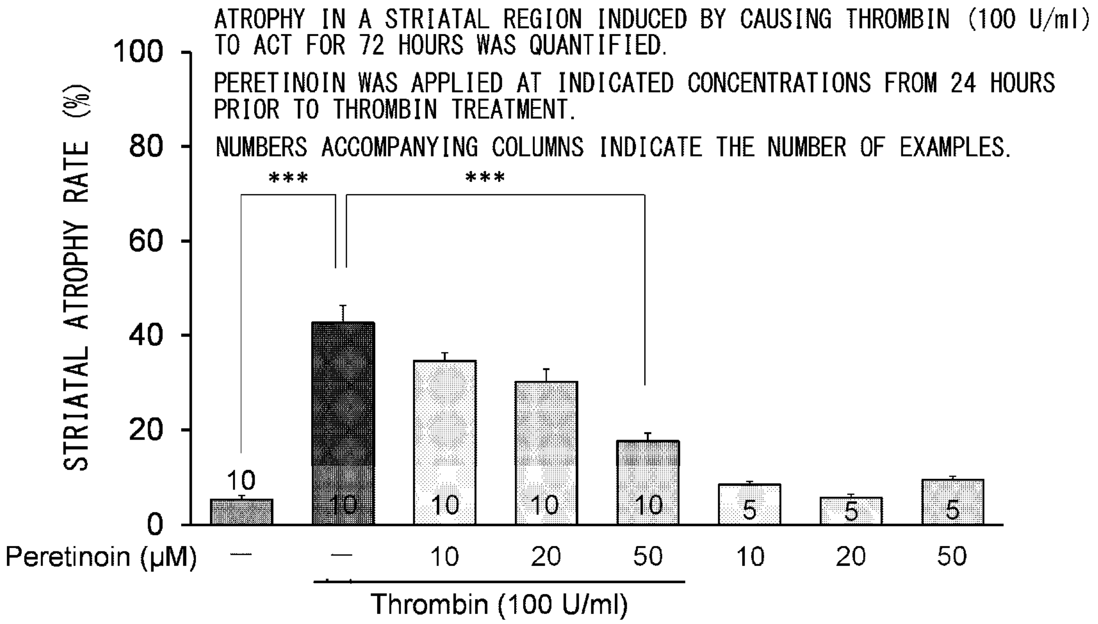
FIG. 8 is a graph showing a rate of striatal tissue atrophy induced by thrombin.

The PI fluorescence images 72 hours after the start of the thrombin treatment are shown in FIG. 6. From this drawing, it was found that even in a case where the thrombin was given, fluorescence became weaker as the concentration increased to 10 μM, 20 μM, and 30 μM in a case where the peretinoin 3 was given at the same time, and that brain tissue disorders caused by the thrombin was suppressed by the peretinoin 3. Further, a rate of cerebral cortex cell death induced by the thrombin obtained from these images is shown in FIG. 7, and a rate of striatal tissue atrophy is shown in FIG. 8. From the graphs of FIGS. 7 and 8, it was found that in cerebral cortex-striatal tissue sections, the cerebral cortex cell death and the striatal tissue atrophy induced by the thrombin were concentration-dependent and significantly suppressed by the peretinoin 3.

(Evaluation Using K252a)

K252a (3 μM) is known to inhibit TrkB, a receptor of a neurotrophic factor BDNF. Therefore, how K252a affects a cytoprotective effect of the peretinoin 3 was examined by the same method as the method of examining the effect on the thrombin toxicity.

Results

Figure 9:
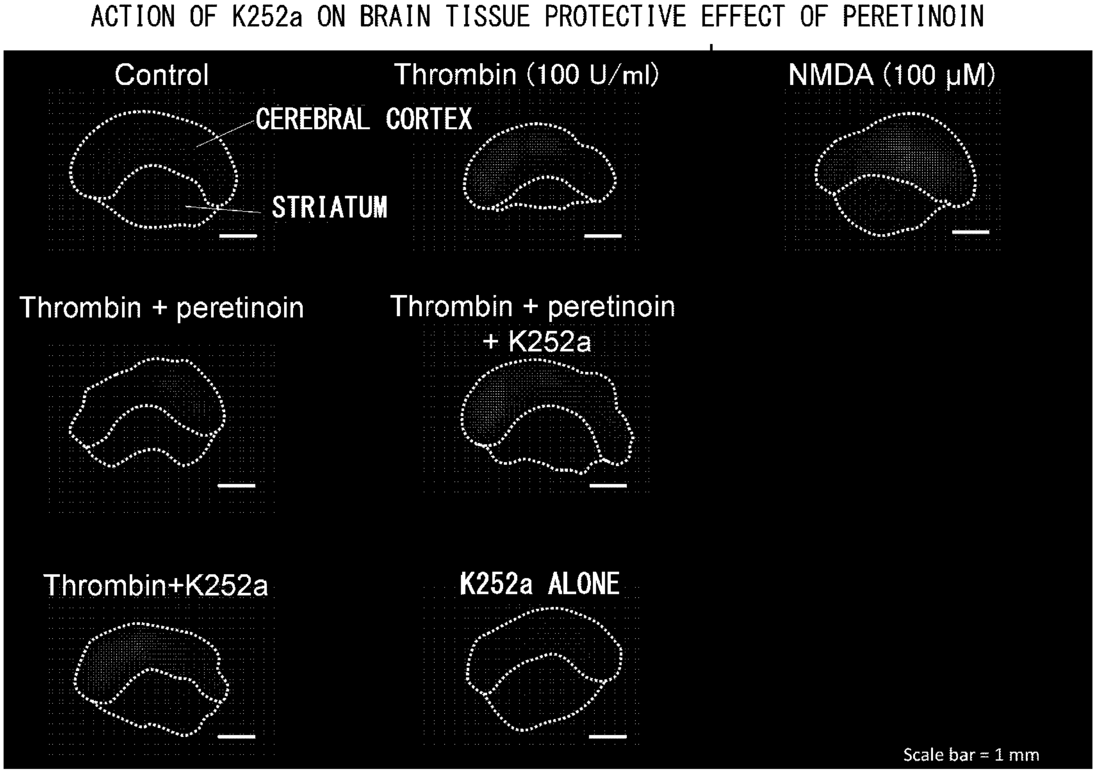
FIG. 9 is PI fluorescence images showing an action of K252a on a protective effect of the peretinoin 3 on brain tissue.
Figure 10:
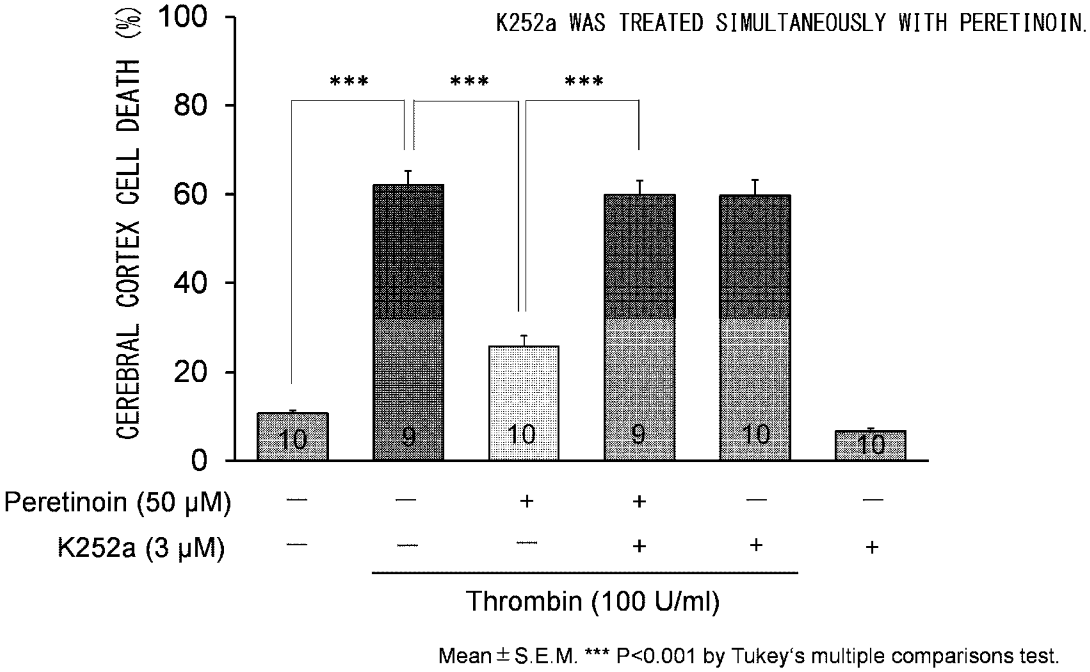
Figure 11:
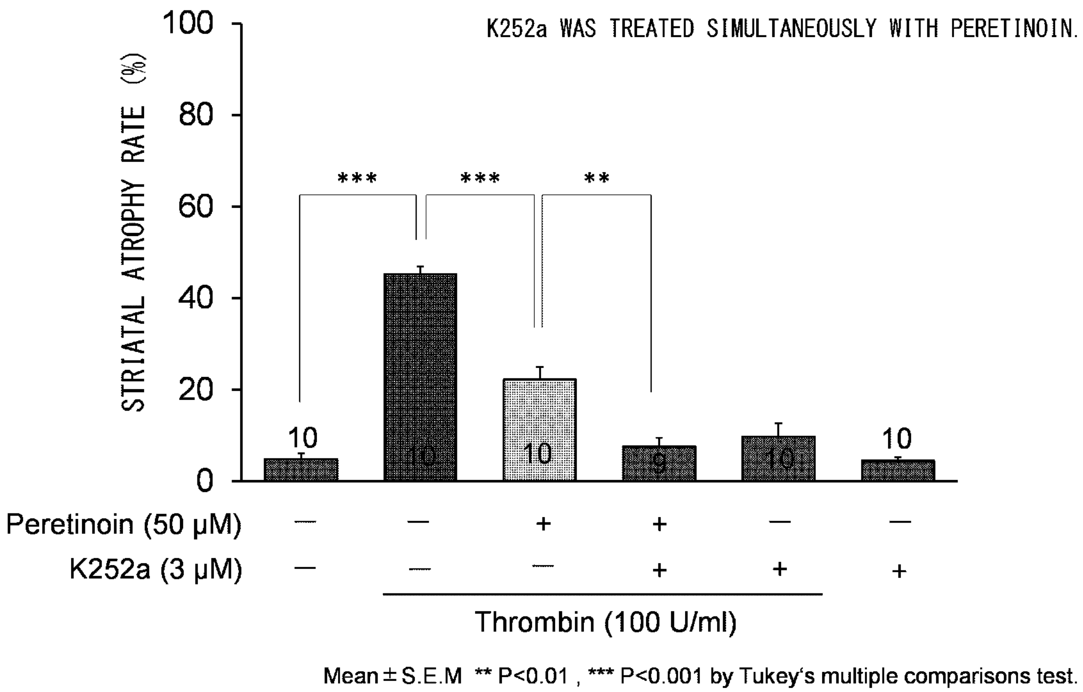

PI fluorescence images after an experiment was conducted under conditions of control, administration of only thrombin, administration of thrombin+peretinoin 3, administration of thrombin+peretinoin 3, administration of thrombin+peretinoin 3+K252a, administration of thrombin+K252a, and administration of only K252a are shown in FIG. 9. Furthermore, a rate of cerebral cortex cell death obtained from these images is shown in FIG. 10, and a rate of striatal tissue atrophy is shown in FIG. 11. The following was found from FIGS. 9, 10, and 11. In other words, 1) since a protective effect of the peretinoin 3 on cerebral cortex cells was blocked by K252a, an involvement of a BDNF-TrkB signaling system is suggested. 2) Since an inhibitory effect of the peretinoin 3 on striatal atrophy was not blocked by K252a, it is suggested that it is due to a mechanism other than the BDNF-TrkB signaling system. In other words, it is considered that the peretinoin 3 exerts a cell and tissue protective effect via different action mechanisms in the cerebral cortex and striatum.

(Effect on Cerebral Hemorrhage Pathology)

A male ICR mouse aged 8 to 10 weeks was placed in a brain stereotaxic apparatus under triple anesthesia, and bleeding was induced by injecting 0.035 U of collagenase type VII (Sigma) into a fixed coordinate (2.3 mm lateral to a median, 0.2 mm posterior to a bregma suture, 3.5 mm below a skull) in the striatum over 2.5 minutes using a 30 gauge needle. After that, the surface of the skull was reduced with dental cement, and breeding was continued. The peretinoin 3 (40 mg/kg) was suspended in water together with 0.5% carboxymethyl cellulose, and administered intragastrically using an oral sonde three times in total 3, 27, and 51 hours after the bleeding induction. Note that for comparison, 0.5% carboxymethyl cellulose without the peretinoin 3 was also administered intragastrically in a similar manner. A degree of motor dysfunction in the mouse was evaluated by performing two types of motor function tests (beam walking test, modified limb-placing test) 6, 24, 48, and 72 hours after the bleeding induction. Further, after completion of the motor function test 72 hours later, the mouse was perfused and fixed under anesthesia, and the brain was extracted to prepare a frozen coronary section having a thickness of 16 μm. The effects of the peretinoin 3 were evaluated by identifying microglia, astrocytes, and neurons in the brain tissue, respectively, through immunohistochemistry using antibodies against Iba1, GFAP, and NeuN, and quantifying the number of cells in a given area or an immune reaction positive area.

(Results)

Figure 12:
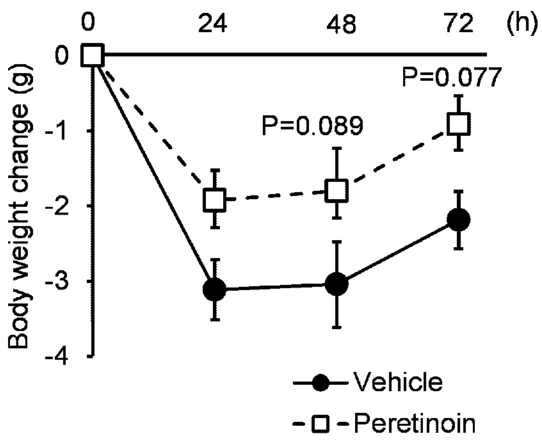
FIG. 12 is a graph showing changes in body weight of a mouse during a motor function test.

Changes in body weight during the test are shown in FIG. 12. Here, the term "Vehicle" indicates a case where 0.5% carboxymethyl cellulose that does not contain the peretinoin 3 is administered. From this drawing, it was shown that the peretinoin 3 suppressed weight loss in the mouse after cerebral hemorrhage.

Figure 13:
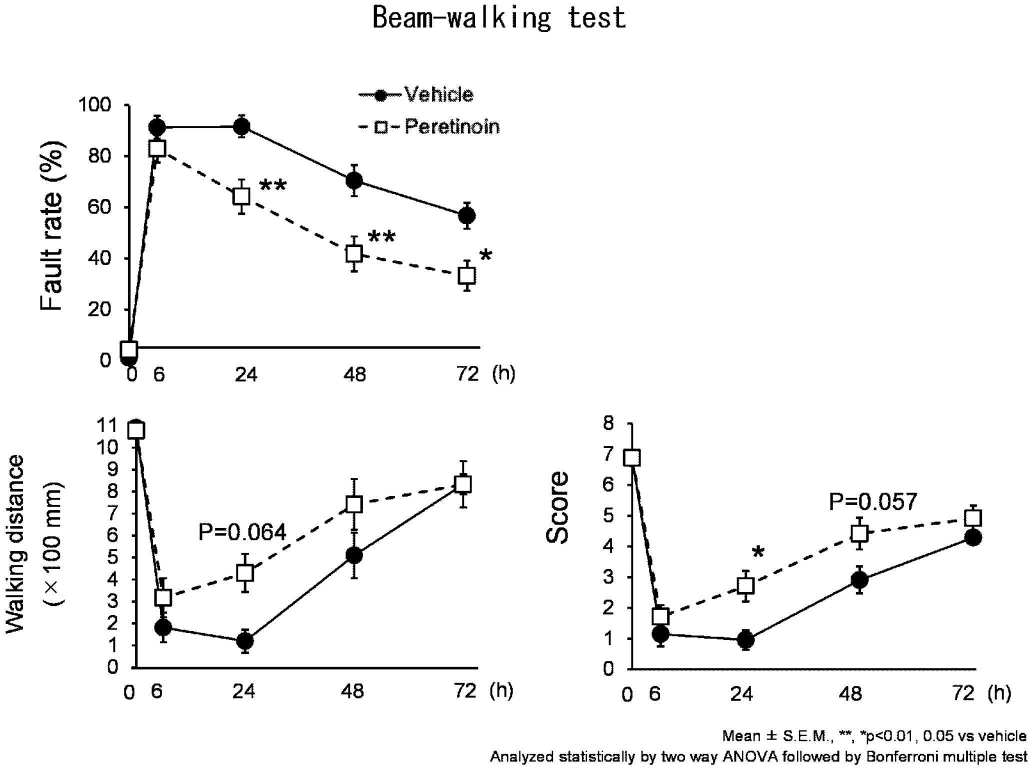
FIG. 13 is graphs showing results of a beam-walking test.

Further, in the beam-walking test, as shown in FIG. 13, the administration of the peretinoin 3 showed a decrease in a fall rate, an increase in a walking width, and an increase in a score.

Figure 14:
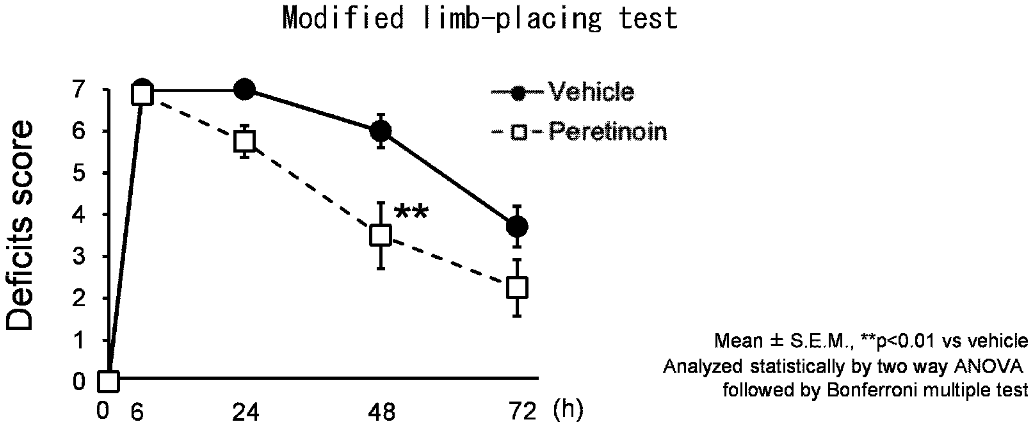
FIG. 14 is a graph showing results of a modified limb-placing test.

Furthermore, in the modified limb-placing testdeha, as shown in FIG. 14, the administration of the peretinoin 3 showed a decrease in a deficit score.

From the above results, it was found that the peretinoin 3 significantly alleviated the motor dysfunction 24 to 72 hours after bleeding.

Figure 15:
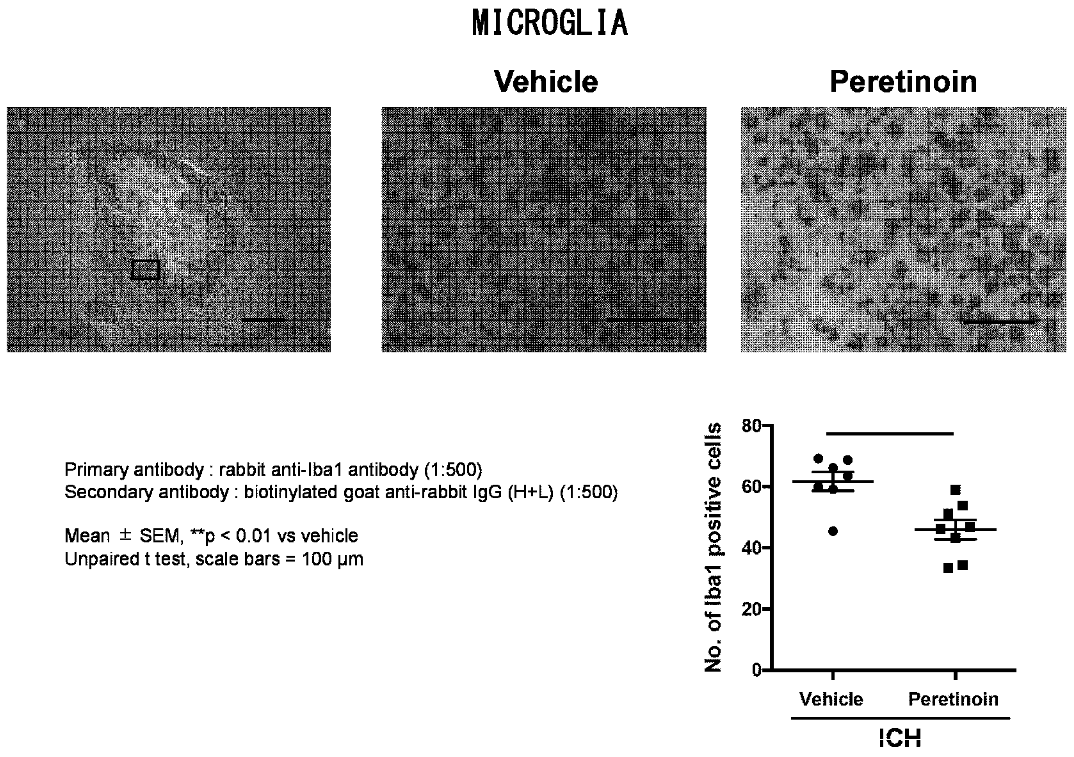
FIG. 15 is images of microglia of brain tissue after completion of the motor function test and a graph showing evaluation thereof.
Figure 16:
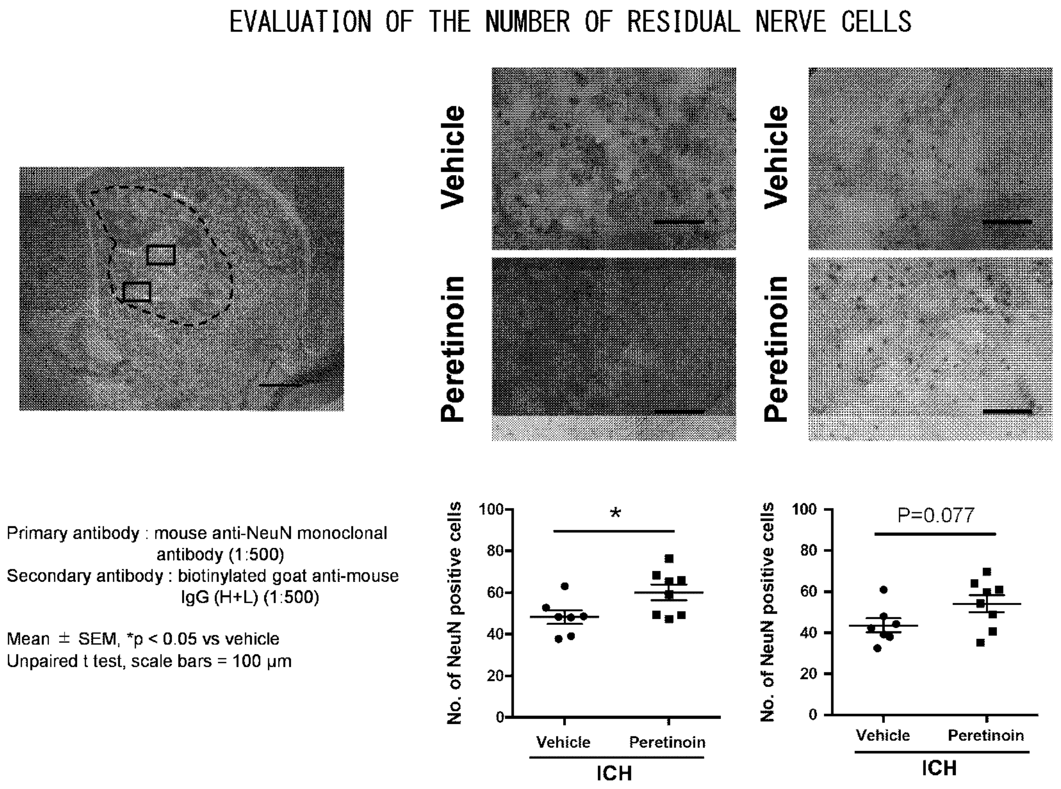
FIG. 16 is images of nerve cells after the completion of the motor function test and graphs showing evaluation of nerve cell shedding.

Further, results of observation of the brain tissue by immunohistochemistry after the completion of the motor function test are shown in FIGS. 15 and 16. From FIG. 15, it was found that the peretinoin 3 significantly suppressed accumulation of activated microglia around a hematoma. In addition, it was found from FIG. 16 that the peretinoin 3 suppressed shedding of nerve cells in the hematoma. The above results suggest a possibility of the peretinoin 3 as a therapeutic drug for cerebral hemorrhage.

<Experiment Showing Differentiation Induction from Stem Cells to Nerve Cells>

The following experiment was performed to examine whether the peretinoin 3 shows the differentiation induction from stem cells to nerve cells as ATRA.

NTERA-2 cl.D1 [NT2/D1] cells (ATCC CRL-1973) (hereinafter described as "NT2 cells") derived from human pluripotent embryonic cancer were adhesion cultured in a maintenance culture medium (high glucose D-MEM (Sigma-Aldrich, D6429), 10% FBS, 100 U/ml penicillin/streptomycin) under conditions of 37° C. and 5% $CO_2$ for 3 to 4 days on a 10 cm plastic dish until becoming confluent. The NT2 cells were exfoliated by Accutase (Innovative Cell Technologies, #AT104), passaged, and maintenance cultured for 50 days. The medium was changed three times a week. The maintenance cultured NT2 cells were dispersed in a petri dish for low-attached microorganisms (STAR SDish9015, RIKEN) at a concentration of $1.5\times10^6$ to $2.5\times10^6$/dish, and suspension cultured on a vibrator (100 rpm) under conditions of 37° C. and 5% $CO_2$, and after one day, 1 μM or 10 μM ATRA was added to induce differentiation and form spheroids. After 14 days, the spheroids were recovered, seeded on a 10 cm dish coated with 5 μg/ml poly-D-lysine (PDL) (Sigma-Aldrich)/laminin (LAM) (iMatrix-511, Nippi), and adhesion cultured under conditions of 37° C. and 5% $CO_2$. From the next day, 3 types of cell division inhibitors (10 μM uridine, 10 μM floxuridine, 1 μM AraC) were added and cultured, and after 3 days, the cells were exfoliated, reseeded on a 35 mm dish coated with PDL/LAM at a concentration of $0.1\times10^6$/dish, and cultured for 4 days in the presence of 3 types of cell division inhibitors, thereby inducing differentiation into nerve cells.

After the differentiation induction, the cells were maintenance cultured in BrainPhys (trademark) Neuronal Medium (STEMCELL Technologies) containing 0.2% NeuroCult (trademark) SM1 Neuronal Supplement under conditions of 37° C. and 5% $CO_2$ for 2 to 3 months. The medium was changed by half three times a week. Accordingly, cells positive for a nerve cell marker MAP2 were obtained and were defined as NT2-N cells.

In order to confirm a statement of synaptic receptors in mature cells, a calcium influx via NMDA-type glutamate receptors was measured as follows.

A fluorescent calcium indicator Fluo-8 AM (AAT Bioquest) was dissolved in Mg-free HHBS (Hepes-buffered Hanks' balanced salt solution (1.26 mM $CaCl_2$, 5.33 mM KCl, 0.44 mM $KH_2PO4$, 4.17 mM $NaHCO_3$, 137.93 mM NaCl, 0.34 mM $Na_2HPO_4$, 5.56 mM D-glucose, 20 mM HEPES, pH 7.4)) containing 0.1 μM glycine (4 μM, 2 μM, respectively). This solution (1 ml) was loaded into NT2-N cells under conditions of 37° C. and 5% $CO_2$ (2 hours, 30 minutes, respectively), and fluo8 was loaded into the cells. Thereafter, an extracellular fluid was replaced with Mg-free HHBS containing 0.1 μM glycine, and it was used for the following measurement after being left in an incubator (37° C., 5% $CO_2$) of a living cell time-lapse imaging device (BioStation IM-Q, Nikon) for 1 hour or more. For the NT2-N cells placed in the device, 5 to 10 fields of view to be analyzed were manually set, and for each field of view, fluorescence intensity was continuously recorded every 2 seconds for 5 minutes at an excitation wavelength of 480 nm/a fluorescence wavelength of 520 nm. Further, after a certain period of time elapsed from the start of recording, 100 μl of the 100 μM NMDA solution (Mg-free HHBS containing 0.1 μM glycine) prepared above was administered.

A part of specimens 2 to 3 months after the start of the culture after the induction was fixed with a 4% paraformaldehyde PBS solution (at room temperature for 30 minutes). After the fixation, it was carefully washed with PBS and treated with a 1% Triton-X 100 PBS solution for 10 minutes. After the treatment, it was sufficiently washed with PBS, then blocked with a 1% BSA and 3% normal goat serum PBS solution, immersed in an anti-MAP2 antibody (1:1000, Millipore #AB 5622) and anti-Nestine antibody (1:1000, ab22035) solution, further washed, and then stained with a fluorescently labeled secondary antibody (Jackson immun laboratory, 115-545-146 and 111-585-144, 1:5000 respectively).

Results

Figure 17:
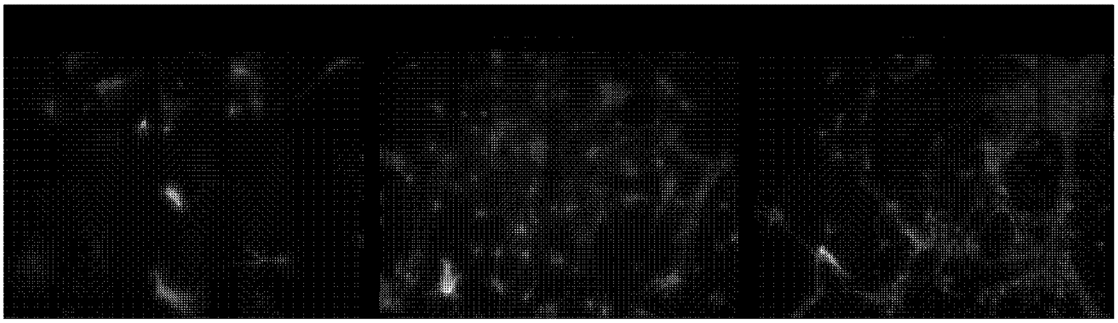
FIG. 17 is images showing differentiation induction from stem cells to nerve cells.
Figure 18:
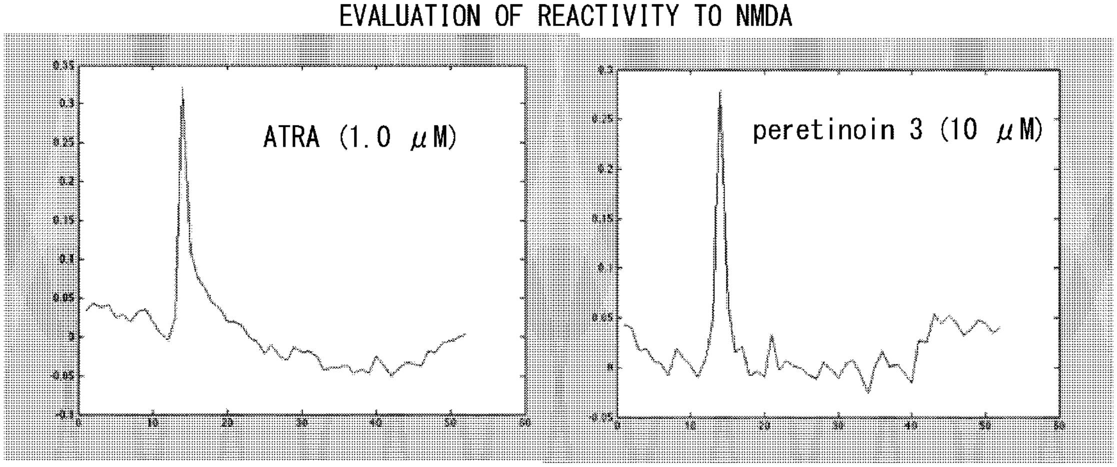
FIG. 18 is graphs which evaluate reactivity to NMDA.

As shown in FIG. 17, similarly to the ATRA, the number of cells expressing MAP2 as a nerve cell marker without expressing nestin as a neuronal precursor cell marker increased by the administration of 10 μM of the peretinoin 3, and the differentiation induction into nerve cells was observed. Further, calcium imaging shown in FIG. 18 suggested that the nerve cells induced to differentiate by the ATRA and the peretinoin 3 expressed NMDA-type glutamate receptors, thereby forming synapses.

The present invention is not limited at all to the description of the embodiments and the examples of the invention described above. Various modifications that can be easily conceived by a person skilled in the art without departing from the scope of the claims are also included in the present invention.

INDUSTRIAL APPLICABILITY

The $^{11}C$-labeled cyclic retinoid of the present invention can be synthesized in a short time with a high yield, and can be suitably used as a PET probe for elucidating the intracerebral kinetics. Further, the central nervous system activator of the present invention can be used as a therapeutic agent for central nervous system degenerative diseases and a lead compound therefor.

The invention claimed is:

1. A $^{11}C$-labeled acyclic retinoid comprising a compound represented by a following chemical formula (a), or an ester or a salt of the compound,

[Chemical formula 1]

(a)

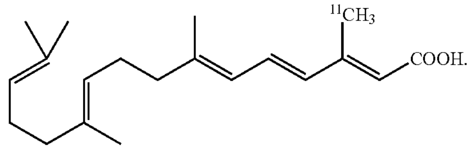

2. A PET probe containing the $^{11}C$-labeled acyclic retinoid of claim 1.

3. A method for producing the $^{11}C$-labeled acyclic retinoid according to claim 1, the method comprising a coupling step of cross-coupling a methyl iodide labeled with $^{11}C$ and a following organotin compound (b), provided that in the formula, —$COOR^1$ represents an ester group wherein $R^1$ is an alkyl or benzyl group and $R^2$ represents an alkyl group, in an aprotic solvent in presence of a palladium complex, a phosphine ligand, and a cuprous halide,

[Chemical formula 2]

(b)

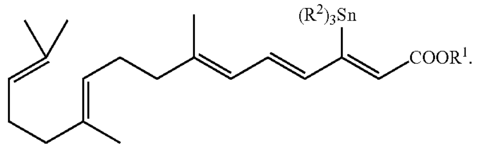

4. A method for treating cerebral hemorrhage or providing neuroprotective effects to the brain, said method comprising administering to a patient in need thereof a central nervous system activator containing an acyclic retinoid represented by the following chemical formula (c), or an ester or a salt of the acyclic retinoid as an active ingredient,

[Chemical formula 3]

(c)

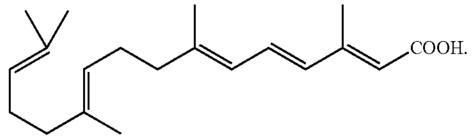

* * * * *